(12) United States Patent
Kishimoto

(10) Patent No.: US 10,958,898 B2
(45) Date of Patent: Mar. 23, 2021

(54) IMAGE CREATION DEVICE, METHOD FOR IMAGE CREATION, IMAGE CREATION PROGRAM, METHOD FOR DESIGNING EYEGLASS LENS AND METHOD FOR MANUFACTURING EYEGLASS LENS

(71) Applicant: NIKON-ESSILOR CO., LTD., Tokyo (JP)

(72) Inventor: Takeshi Kishimoto, Tokyo (JP)

(73) Assignee: NIKON-ESSILOR CO., LTD., Tokyo (JP)

( * ) Notice: Subject to any disclaimer, the term of this patent is extended or adjusted under 35 U.S.C. 154(b) by 0 days.

(21) Appl. No.: 16/389,428

(22) Filed: Apr. 19, 2019

(65) Prior Publication Data
US 2019/0246095 A1    Aug. 8, 2019

Related U.S. Application Data

(63) Continuation of application No. PCT/JP2017/037741, filed on Oct. 18, 2017.

(30) Foreign Application Priority Data

Oct. 20, 2016  (JP) ............................. JP2016-205990

(51) Int. Cl.
*H04N 13/332* (2018.01)
*H04N 13/128* (2018.01)
(Continued)

(52) U.S. Cl.
CPC ............ *H04N 13/332* (2018.05); *A61B 3/00* (2013.01); *G02B 27/0172* (2013.01); *G02C 7/00* (2013.01);
(Continued)

(58) Field of Classification Search
CPC ........ H04N 13/332; G06T 7/593; G06T 15/06
See application file for complete search history.

(56) References Cited

U.S. PATENT DOCUMENTS 6,792,401 B1 * 9/2004 Nigro .................... G02C 13/003
703/6
7,275,822 B2 * 10/2007 Gupta ...................... G02C 7/02
351/159.75

(Continued)

FOREIGN PATENT DOCUMENTS

| JP | 2003-177076 | 6/2003 |
| JP | 2010-134460 | 6/2010 |
| WO | WO 2010/044383 A1 | 4/2010 |

OTHER PUBLICATIONS

International Search Report dated Jan. 23, 2018 in corresponding International Patent Application No. PCT/JP2017/037741 (2 pages).
(Continued)

*Primary Examiner* — Terrell M Robinson

(57) ABSTRACT

An image creation device includes: a storage unit in which target scene three-dimensional information related to a position, a shape and optical characteristics of a structural object present in a virtual target scene, eyeglass lens three-dimensional information related to a position, a shape and optical characteristics of an eyeglass lens and eyeball three-dimensional information related to a position, a shape and optical characteristics of an eye of a wearer viewing the target scene through the eyeglass lens used as a virtual lens; and a retina image creation unit that creates a retina image based upon the target scene three-dimensional information, the eyeglass lens three-dimensional information and the eyeball three-dimensional information, wherein: the retina image is a virtual image projected onto a retina of the eye of the wearer viewing the target scene through the eyeglass lens.

14 Claims, 14 Drawing Sheets

(51) Int. Cl.
*G06T 15/06* (2011.01)
*G06K 9/00* (2006.01)
*G06T 7/593* (2017.01)
*G02C 7/02* (2006.01)
*G02B 27/01* (2006.01)
*G06T 7/00* (2017.01)
*G02C 7/00* (2006.01)
*G06T 19/00* (2011.01)
*G02C 13/00* (2006.01)
*A61B 3/00* (2006.01)
*G06F 30/00* (2020.01)
*H04N 13/00* (2018.01)

(52) U.S. Cl.
CPC ............ *G02C 7/025* (2013.01); *G02C 13/00* (2013.01); *G06F 30/00* (2020.01); *G06K 9/00604* (2013.01); *G06T 7/0014* (2013.01); *G06T 7/593* (2017.01); *G06T 15/06* (2013.01); *G06T 19/00* (2013.01); *H04N 13/128* (2018.05); *G02B 2027/0178* (2013.01); *G06T 2207/10012* (2013.01); *G06T 2207/30041* (2013.01); *H04N 2013/0081* (2013.01)

(56) References Cited

U.S. PATENT DOCUMENTS

| | | | | |
|---|---|---|---|---|
| 7,740,358 | B2* | 6/2010 | Pedrono | G02C 7/061 351/159.05 |
| 9,110,312 | B2* | 8/2015 | Encaoua | G02C 13/005 |
| 2003/0076479 | A1* | 4/2003 | Qi | G01M 11/0235 351/233 |
| 2010/0114540 | A1 | 5/2010 | Shinohara et al. | |
| 2011/0217638 | A1* | 9/2011 | Kim | G02B 5/3083 430/20 |
| 2012/0026183 | A1 | 2/2012 | Qi et al. | |
| 2012/0081661 | A1 | 4/2012 | Yamakaji | |
| 2014/0362446 | A1* | 12/2014 | Bickerstaff | G02B 27/017 359/630 |
| 2015/0362761 | A1* | 12/2015 | Adler | G06T 17/00 705/26.5 |
| 2016/0035133 | A1* | 2/2016 | Ye | G06T 19/006 345/419 |
| 2017/0132845 | A1* | 5/2017 | Everman, II | G06T 19/006 |
| 2017/0188808 | A1* | 7/2017 | Quigley | B05D 1/18 |
| 2017/0269353 | A1* | 9/2017 | Xu | G02B 30/27 |
| 2017/0293354 | A1* | 10/2017 | Lu | G06K 9/00604 |
| 2018/0249151 | A1* | 8/2018 | Freeman | G16H 20/30 |

OTHER PUBLICATIONS

Translation by WIPO of the International Preliminary Report on Patentability dated Apr. 23, 2019 in corresponding International Patent Application No. PCT/JP2017/037741 (8 pages).
Extended European Search Report dated Apr. 8, 2020 in European Patent Application No. 17863041.4.
"Correlation and Dependence", Wkipedia, Jun. 13, 2020, https://en.wikipedia.org/wiki/Correlation_and_dependence, 11 pages.
"Spline Interpolation", Wkipedia, May 21, 2020, https://en.wikipedia.org/wiki/Spline_interpolation, 4 pages.
Canadian Office Action dated May 21, 2020 in Canadian Patent Application No. 3,040,852.
Canadian Office Action dated Jan. 25, 2021 in Canadian Patent Application No. 3,040,852.

* cited by examiner

FIG. 3

| INPUT DATA CATEGORY | INFORMATION TYPE | CONTENTS |
|---|---|---|
| OUTSIDE WORLD DESCRIPTION DATA | GEOMETRIC OBJECT TYPE, SHAPE | SPHERE, PLANE, CYLINDRICAL SURFACE, CUBE, COMPOSITE OBJECT, ETC. |
| | GEOMETRIC OBJECT POSITION INFORMATION, GEOMETRIC OBJECT MATERIAL CHARACTERISTICS | INFORMATION WITH RESPECT TO REFLECTANCE TRANSMITTANCE, COLOR, TEXTURE, ETC. |
| | LIGHTING INFORMATION | LIGHTING POSITION, ILLUMINATING LIGHT COLOR, WAVELENGTH DISTRIBUTION, LIGHT INTENSITY, ETC. |
| | GAZING POINT INFORMATION | GAZING POINT POSITION, ETC. |
| EYEBALL DESCRIPTION DATA | GEOMETRIC INFORMATION PERTAINING TO EYEBALL STRUCTURE | POSITIONS, RADII OF CURVATURE OF LENS, RETINA, CORNEA AND PUPIL, PUPIL DIAMETER, ETC. |
| | EYEBALL STRUCTURE MATERIAL CHARACTERISTICS INFORMATION | REFRACTIVE INDEX, ETC. |
| | RETINA INFORMATION | RETINA PROJECTION RANGE, ETC. |
| | POSITION INFORMATION PERTAINING TO EYEBALL MODEL | POSITION, ORIENTATION AND THE LIKE OF EYEBALL MODEL |
| EYEGLASS LENS DESCRIPTION DATA | GEOMETRIC INFORMATION PERTAINING TO EYEGLASS LENS | EXTERNAL SHAPE INFORMATION, CENTRAL THICKNESS, SPLINE FUNCTIONS OF ANTERIOR AND POSTERIOR SURFACES AND PERIPHERAL SURFACES, ETC. |
| | EYEGLASS LENS MATERIAL CHARACTERISTICS INFORMATION | REFRACTIVE INDEX, ETC. |
| | EYEGLASS LENS MODEL POSITION INFORMATION | POSITION, ORIENTATION AND THE LIKE OF EYEGLASS LENS MODEL |

IMAGE CREATION DEVICE, METHOD FOR IMAGE CREATION, IMAGE CREATION PROGRAM, METHOD FOR DESIGNING EYEGLASS LENS AND METHOD FOR MANUFACTURING EYEGLASS LENS

This application is a continuation of International Application No. PCT/JP2017/037741 filed Oct. 18, 2017, which claims priority benefit to Japanese Patent Application No. 2016-205990, filed Oct. 20, 2016, the disclosures of which are hereby incorporated in their entirety by reference.

TECHNICAL FIELD

The present invention relates to an image creation device, an image creation method, an image creation program, a method for designing an eyeglass lens and a method for manufacturing an eyeglass lens.

BACKGROUND ART

There is a method in the known art, through which an image, indicating binocular view performance achieved when a field of vision is observed through eyeglass lenses by rotating both eyes onto various object points in the field of vision, is displayed (see PTL 1). However, the image indicating the binocular view performance displayed through the method, does not encompass an entire field of vision that is projected onto retinas.

CITATION LIST

Patent Literature

PTL 1: Japanese Laid Open Patent Publication No. 2003-177076

SUMMARY OF INVENTION

According to the 1st aspect of the present invention, an image construction device comprises: a storage unit in which target scene three-dimensional information related to a position, a shape and optical characteristics of a structural object present in a virtual target scene, eyeglass lens three-dimensional information related to a position, a shape and optical characteristics of an eyeglass lens and eyeball three-dimensional information related to a position, a shape and optical characteristics of an eye of a wearer viewing the target scene through the eyeglass lens used as a virtual lens; and a retina image creation unit that creates a retina image based upon the target scene three-dimensional information, the eyeglass lens three-dimensional information and the eyeball three-dimensional information, wherein: the retina image is a virtual image projected onto a retina of the eye of the wearer viewing the target scene through the eyeglass lens.

According to the 2nd aspect of the present invention, it is preferred that the image construction device according to the 1st aspect further comprises: a corresponding point calculation unit that calculates corresponding points, in retina images of two eyes, the corresponding points corresponding to a position within the target scene; and a disparity calculation unit that calculates a binocular disparity with respect to the position based upon the corresponding points.

According to the 3rd aspect of the present invention, in the image construction device according to the 2nd aspect, it is preferred that the corresponding point calculation unit calculates the corresponding points based upon correlation coefficients with respect to, or differences between, luminance values at pixels in a first pixel region where a plurality of pixels are present, set in the retina image for one eye, and luminance values at pixels in a second pixel region where a plurality of pixels are present, set in the retina image for another eye.

According to the 4th aspect of the present invention, it is preferred that the image construction device according to the 2nd or the 3rd aspect further comprises a composite image creation unit that creates a composite image by using the retina images for the two eyes based upon the binocular disparity and a disparity correction parameter that includes a fusion ratio.

According to the 5th aspect of the present invention, it is preferred that the image construction device according to any one of the 2nd to 5th aspects further comprises: a disparity display unit that displays a distribution of the binocular disparity, which corresponds to the retina images.

According to the 6th aspect of the present invention, in the image construction device according to any one of the 1st to the 5th aspect, it is preferred that the retina image creation unit comprises a correction image creation unit that creates the retina image projected onto each retina of the eye based upon corrective lens three-dimensional information related to a position, a shape and optical characteristics of a corrective lens.

According to the 7th aspect of the present invention, it is preferred that the image construction device according to any one of the 1st to 6th aspects further comprises: a ray tracing unit that calculates an entry direction along which, and an entry position at which a ray of light entering the retina of the eye at each position, enters an anterior surface of a cornea of the eye and calculates a light path along which the ray of light, having departed the target scene, passes through the anterior surface of the cornea and arrives at the position in the retina, and a luminance value at a pixel corresponding to the position in the retina, based upon the entry direction and the entry position.

According to the 8th aspect of the present invention, it is preferred that the image construction device according to any one of the 1st to 7th aspects further comprises: an eyeball shape calculation unit that calculates the shape and the optical characteristics of the eye of the wearer based upon prescription data pertaining to the wearer.

According to the 9th aspect of the present invention, in the image construction device according to the 8th aspect, it is preferred that the eyeball shape calculation unit calculates the shape of the eye based upon accommodation ability and a pupil diameter of the wearer.

According to the 10th aspect of the present invention, it is preferred that the image construction device according to any one of the 1st to 9th aspects further comprises: a moving image display unit that displays the retina image, or a composite image created by using the retina images for two eyes, as a moving image based upon a change occurring in the eyeball three-dimensional information.

According to the 11th aspect of the present invention, a method for image creation comprises: creating a retina image based upon target scene three-dimensional information related to a position, a shape and optical characteristics of a structural object in a virtual target scene, eyeglass lens three-dimensional information related to a position, a shape and optical characteristics of an eyeglass lens and eyeball three-dimensional information related to a position, a shape and optical characteristics of an eye of a wearer virtually viewing the target scene through the eyeglass lens, wherein:

the retina image is an image of the target scene virtually viewed by the wearer through the eyeglass lens, projected onto a retina of the eye of the wearer.

According to the 12th aspect of the present invention, in the method for image creation according to the 11th aspect, it is preferred that creating a composite image by using retina images of the two eyes based upon a disparity correction parameter that sets an extent by which a binocular disparity of the two eyes is to be corrected.

According to the 13th aspect of the present invention, an image creation program enables a computer to execute: retina image creation processing through which a retina image is created based upon target scene three-dimensional information related to a position, a shape and optical characteristics of a structural object in a virtual target scene, eyeglass lens three-dimensional information related to a position, a shape and optical characteristics of an eyeglass lens and eyeball three-dimensional information related to a position, a shape and optical characteristics of an eye of a wearer virtually viewing the target scene through the eyeglass lens, wherein: the retina image is an image of the target scene virtually viewed by the wearer through the eyeglass lens, projected onto a retina of the eye of the wearer.

According to the 14th aspect of the present invention, a method for designing an eyeglass lens comprises: designing an eyeglass lens based upon the shape of the eyeglass lens used by the image creation device according to any one of the 1st through 10th aspects, to create the retina image.

According to the 15th aspect of the present invention, a method for manufacturing an eyeglass lens, comprises: designing the eyeglass lens through the method for designing an eyeglass lens according to the 14th aspect; and manufacturing the eyeglass lens having been designed through the method for designing an eyeglass lens.

BRIEF DESCRIPTION OF DRAWINGS

FIG. 3 is a chart of a structure that may be adopted for input data, presented in a table format

DESCRIPTION OF EMBODIMENT

The following is a description given in reference to drawings as needed, of an image creation device, an image creation method, an image creation program, a method for designing an eyeglass lens, a method for manufacturing an eyeglass lens and the like achieved in an embodiment. The image creation device in the embodiment creates retina images and a binocular view image of a subject virtually viewed by a wearer.

Figure 1:
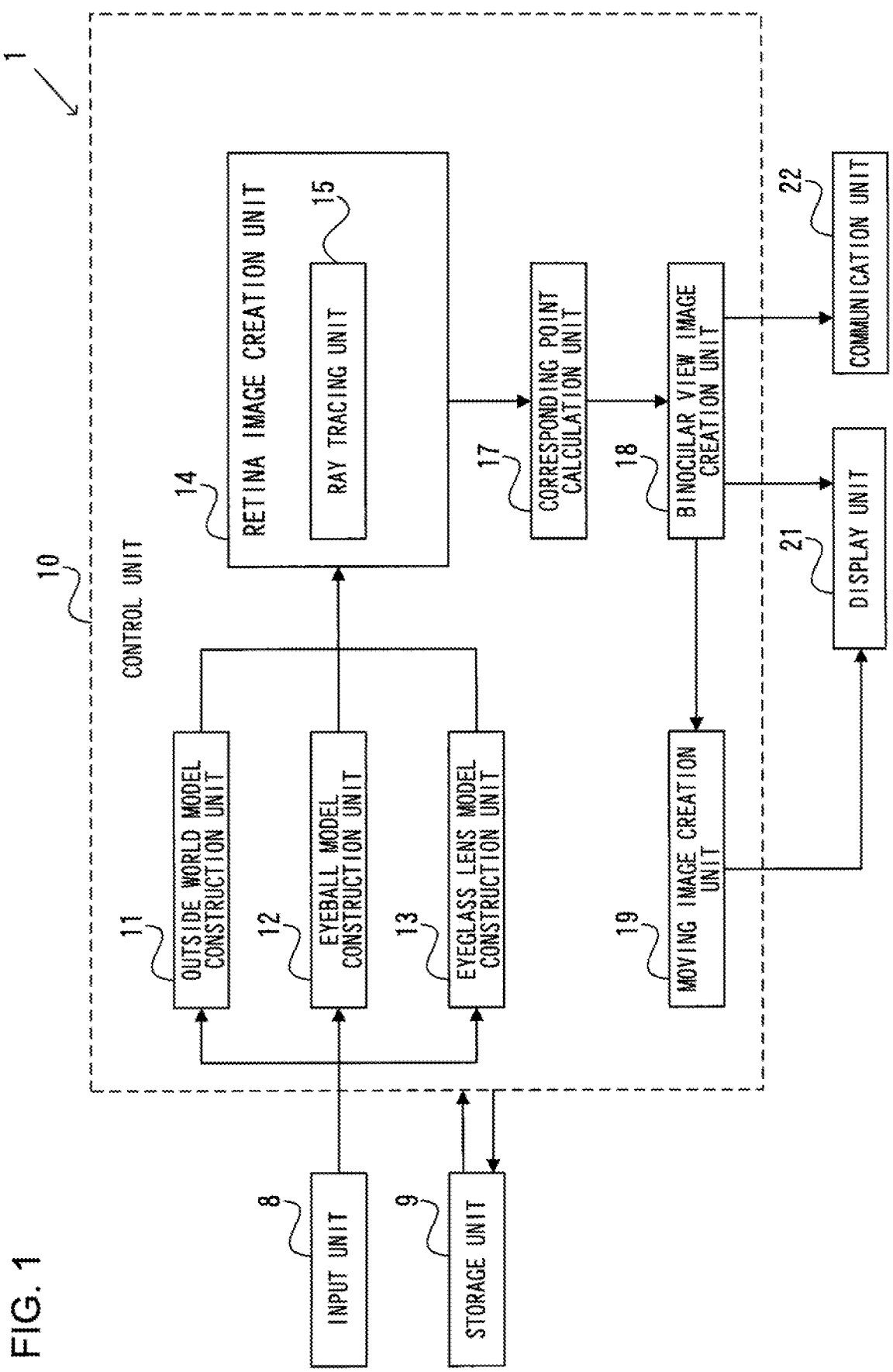
FIG. 1 is a schematic diagram showing a configuration of an image creation device achieved in an embodiment

FIG. 1 is a schematic diagram showing the configuration of an image creation device 1 achieved in the embodiment. The image creation device 1 comprises an input unit 8, a storage unit 9, a control unit 10, a display unit 21 and a communication unit 22. The control unit 10 includes an outside world model construction unit 11, an eyeball model construction unit 12, an eyeglass lens model construction unit 13, a retina image creation unit 14, a corresponding point calculation unit 17, a binocular view image creation unit 18 and a moving image creation unit 19. The retina image creation unit 14, in turn, includes a ray tracing unit 15. The arrows in FIG. 1 indicate primary flows of information pertaining to image creation.

The input unit 8, configured with an input device such as a keyboard, accepts entry of input data and the like, which are needed in processing executed in the outside world model construction unit 11, the eyeball model construction unit 12 and the eyeglass lens model construction unit 13, as will be explained later. The input unit 8 outputs the input data to the outside world model construction unit 11, the eyeball model construction unit 12 and the eyeglass lens model construction unit 13 in the control unit 10.

It is to be noted that input data may instead be received at the communication unit 22, which will be described later, and then may be output to the control unit 10. There are no particular restrictions imposed with regard to the method through which input data are entered, and data stored in advance in the storage unit 9 may be used as the input data.

The storage unit 9, constituted with a non-volatile storage medium such as a memory or a hard disk, exchanges data with the control unit 10 so as to store various types of data such as the input data having been entered via the input unit 8, a model obtained through processing executed in the control unit 10, retina images and a binocular view image to be explained later, and the like.

The control unit 10, which is configured with a CPU or the like, functions as an executioner engaged in operation of controlling the image creation device 1 and executes various types of processing, including image creation processing, by executing a program installed in the storage unit 9 or in a non-volatile memory included in the control unit 10.

The outside world model construction unit 11 constructs an outside world model by setting geometric objects in correspondence to three-dimensional coordinate points based upon outside world description data (see FIG. 3) that are a type of input data entered via the input unit 8. The outside world model construction unit 11 outputs a three-dimensional outside world model it has constructed to the retina image creation unit 14. While the embodiment will be explained in reference to an example in which a model of an indoor scene is used as the outside world model, with rectangular parallelepiped and cylindrical objects that look like a desk, a chair and the like, set therein (see FIG. 4), there are no particular restrictions imposed with regard to the contents of the outside world model as long as the contents are described in three dimensions.

It is to be noted that the term "scene" used in the description of the embodiment simply refers to an outside world that can be viewed and no particular restrictions are imposed with respect to its contents.

The eyeball model construction unit 12 constructs three-dimensional models of eyeballs by using eyeball description data (see FIG. 3) that are a type of input data entered via the input unit 8, and outputs the three-dimensional eyeball models to the retina image creation unit 14 together with position information indicating the positions of the eyeball models within the outside world model.

The eyeglass lens model construction unit 13 constructs three-dimensional models of eyeglass lenses by using eyeglass lens description data (see FIG. 3) that are a type of input data entered via the input unit 8, and outputs the three-dimensional eyeglass lens models to the retina image creation unit 14 together with position information indicating the positions of the eyeglass lens models within the outside world model.

The retina image creation unit 14 creates retina images based upon data representing the outside world model input thereto from the outside world model construction unit 11, data representing the eyeball models and the position information of the eyeball models in the outside world model input thereto from the eyeball model construction unit 12, and data representing the eyeglass lens models and the position information of the eyeglass lens models in the outside world model input thereto from the eyeglass lens model construction unit 13. The term "retina image" used in the description of the embodiment refers to a virtual image of a scene virtually viewed by a wearer through an eyeglass lens, projected onto either of the retinas in the eyes of the wearer.

The ray tracing unit 15 in the retina image creation unit 14 calculates the luminance of light entering the retina in each of the eyeball models at a given position through two-stage ray tracing. In the first stage, it traces the incident light ray along the reverse direction from each position in the retina in each eyeball model so as to calculate the corresponding incident light position at the anterior surface of the cornea in the eyeball model and the direction of the entry at the cornea anterior surface. In the second stage, the incident light at the cornea anterior surface, the position and the direction of which have been calculated in the first stage, is traced along the reverse direction so as to calculate the luminance of light at the corresponding retina position in relation to light scattered at the corresponding object point in the outside world model. The ray tracing unit 15 outputs retina images corresponding to the two eyes to the corresponding point calculation unit 17.

The corresponding point calculation unit 17 calculates corresponding points in the left and right retina images, based upon correlation coefficients or differences with respect to the pixel values representing the retina images for the two eyes. The term "corresponding points" in this context refers to the position in the left-eye retina image and the position in the right-eye retina image at which light from a given object point in the outside world model enters. In addition, the corresponding point calculation unit 17 calculates the difference between a pixel position (x, y) of the corresponding point in the left-eye retina image and the pixel position (x, y) of the corresponding point in the right-eye retina image as a disparity. The corresponding point calculation unit 17 outputs the retina images for the two eyes and information indicating a plurality of pairs of corresponding points on the retina images and disparities for the pairs of corresponding points, to the binocular view image creation unit 18.

The corresponding point calculation unit 17 can create a disparity display image indicating the disparity distribution in a binocular view image before disparity correction and/or a binocular view image after disparity correction. In addition, the corresponding point calculation unit 17 is able to output a disparity display image having been created to the display unit 21 so as to bring it up on display, to the communication unit 22 so as to transmit it to an external device, to the moving image creation unit 19 so as to create a moving image, and to the storage unit 9 as needed, so as to have it stored in the storage unit 9.

The binocular view image creation unit 18 creates a binocular view image based upon the retina images for the two eyes, and the information indicating the corresponding points and the disparity, input thereto from the corresponding point calculation unit 17. The binocular view image creation unit 18 can alter a disparity correction quantity, i.e., an extent of disparity correction, depending on positions in the retina image, in conjunction with a disparity correction parameter used as a disparity correction quantity index. The binocular view image creation unit 18 can output the binocular view image having been created to the display unit 21 so as to bring it up on display, to the communication unit 22 so as to transmit it to an external device, to the moving image creation unit 19 so as to create a moving image and to the storage unit 9 as needed, so as to have it stored in the storage unit 9.

The moving image creation unit 19 creates a moving image in conjunction with images input thereto from the binocular view image creation unit 18 or the storage unit 9, which indicates changes occurring in a retina image, a binocular view image, a disparity display image or the like resulting from changes made over time in the data constituting the input data or various parameters such as the disparity correction parameter. The moving image creation unit 19 can output the moving image having been created to the display unit 21 so as to bring it up on display, to the communication unit 22 so as to transmit it to an external device, and to the storage unit 9 as needed, so as to have it stored in the storage unit 9.

The display unit 21, configured with a device capable of image display such as a liquid crystal monitor, displays an image input thereto from the binocular view image creation unit 18, the moving image creation unit 19 or the like. The communication unit 22, configured with a communication device capable of carrying out communication via the Internet or the like, transmits an image created by the image creation device 1 and transmits/receives necessary data when needed.

It is to be noted that the various functions of the control unit 10 may be fulfilled in a plurality of separate devices and the image creation processing described above may be executed in an overall system configured with these devices, which exchange information with one another. In addition, the storage unit 9, the display unit 21 and the communication unit 22 may be configured with external devices located outside the image creation device 1.

Figure 2:
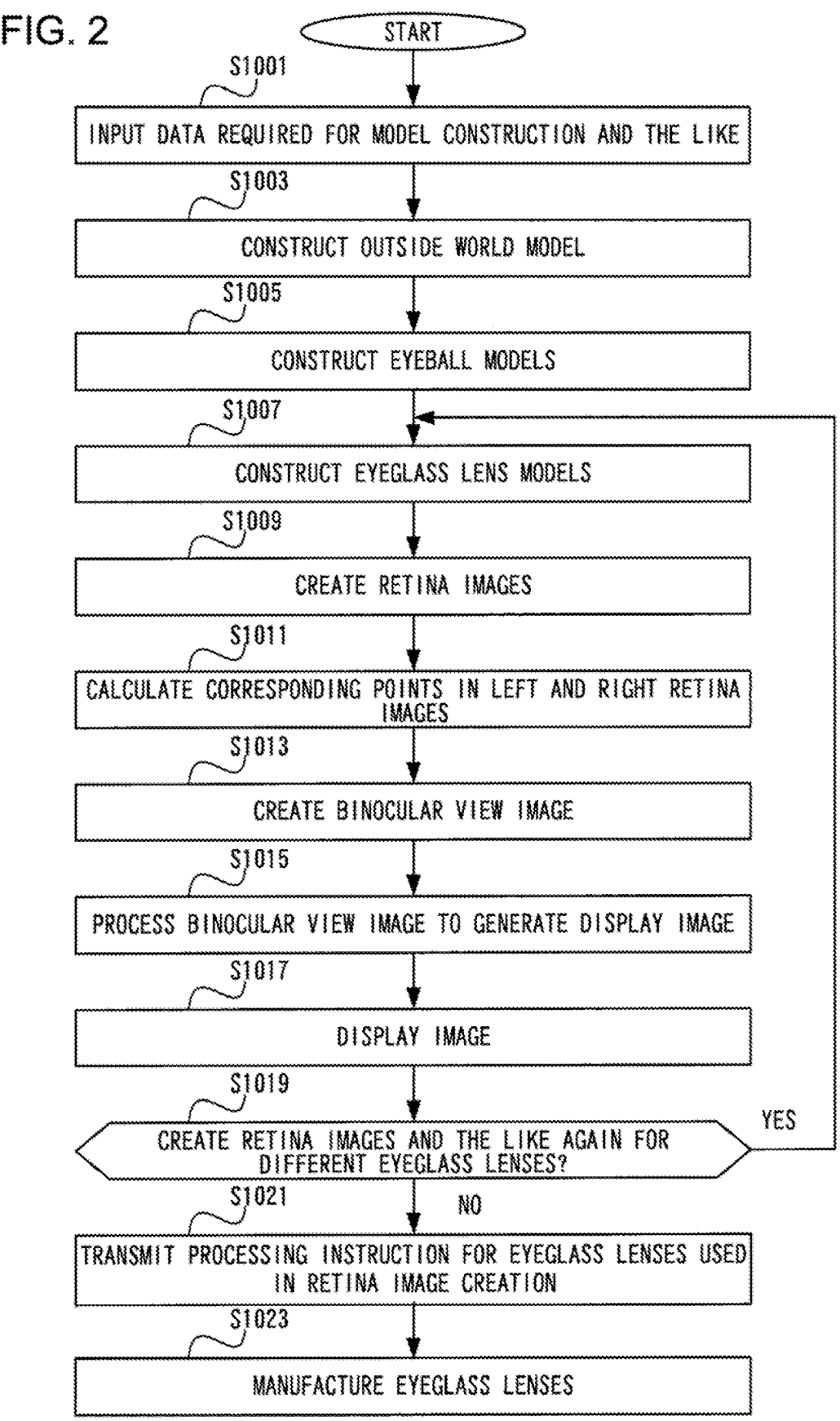
FIG. 2 is a flowchart of an image creation method adopted in the image creation device in the embodiment

FIG. 2 presents a flowchart pertaining to the image creation method adopted in the image creation device and the process of designing and manufacturing eyeglass lenses in the embodiment. The following is a detailed description of the image creation method and the like, given in reference to the flowchart presented in FIG. 2.

In step S1001, the input data required for model construction are taken into the input unit 8.

FIG. 3 shows the structure of the input data. The input data include the outside world description data that define the contents of an outside world model, the eyeball description data that define the contents of eyeball models and the eyeglass lens description data that define the contents of eyeglass lens models.

It is to be noted that the data included in the input data are not limited to the examples presented in FIG. 3. In addition, some of the data in FIG. 3 may each take a predetermined fixed value, and the data design may be modified as needed.

The outside world description data have a structure that includes data used by the outside world model construction unit 11 for constructing an outside world model. They include information indicating categories and shapes of geometric objects disposed in the outside world model, position information indicating the positions of the geometric objects, material characteristics information, lighting information, gazing point information and the like. The geometric objects include geometric elements such as a sphere, a plane, a cylindrical surface and a cube, and composite objects representing structural bodies such as a wall, a desk and a chair, which are defined as composites of geometric elements. In this example, geometric objects are classified into two categories, i.e., geometric elements and composite objects. Position information, set in correspondence to each geometric object, indicates the position and the orientation of each geometric object in the outside world model, and information indicating the reflectance and transmittance of light at the surface of the geometric object, the color and the texture of the geometric object, and the like is also set in correspondence to each geometric object. Fine three-dimensional structural details of a given geometric object may be expressed through substitution with information about a plane of geometric object as texture. The lighting information indicates the position of the illuminating light source, the color of the illuminating light, the wavelength distribution, the light intensity and the like. The gazing point information indicates a gazing point position and the like.

The eyeball description data have a structure that includes data used by the eyeball model construction unit 12 for constructing eyeball models, and are made up with geometric information pertaining to the eyeball structures of the wearer, eyeball structure material characteristics information of the wearer, retina information, position information pertaining to the eyeball model and the like. The geometric information pertaining to an eyeball structure indicates the positions of optical elements in an eyeball such as the crystalline lens, the retina, the cornea and the pupil, the radii of curvature of the optical elements, the diameter of the pupil and the like. The eyeball structure material characteristics information indicates optical characteristics such as the refractive indices of the optical elements in the eyeball. The retina information indicates a retina projection range over which the outside world model is projected, and the like. The retina projection range is a range that includes the starting point of ray tracing, through which a ray is traced from the retina along the reverse direction. The position information pertaining to the eyeball model includes position information indicating the positions and the orientations of the eyeball models set in the outside world model.

The eyeglass lens description data include geometric information pertaining to eyeglass lens, eyeglass lens material characteristics information and eyeglass lens model position information. The geometric information pertaining to eyeglass lens includes external shape information of the eyeglass lens, the central thickness thereof and shape data indicating the contours assumed at the anterior surface and the posterior surface, respectively located on the object side and on the eyeball side, and at the surface in peripheral areas of the eyeglass lens. The shape data indicating the contours of the lens surfaces at the eyeglass lens may be described by adopting, for instance, a spline function. The eyeglass lens material characteristics information includes data indicating the refractive index and the like. The eyeglass lens model position information includes position information indicating the position and orientation of each eyeglass lens model set in the outside world model.

A sales clerk, for instance, at an eyeglass store, may obtain prescription data with respect to a wearer, and may enter data required for model construction obtained through measurement conducted at the store. The outside world description data may be obtained by the sales clerk by asking questions related to the wearer's daily routines, the typical environment of his daily life and the like and then by selecting a model among outside world models prepared in advance. Alternatively, the wearer himself may be asked to select a preferred outside world model. Regarding the eyeball model, the data may be obtained via a shape measuring device that measures shapes by using x-rays or the like, known values may be used therefor by referencing Gullstrand's optical schematic eye, or standard average values may be entered data based upon the age, the gender and the like of the wearer. The eyeglass lens description data can be obtained via a designing device through calculation executed based upon the wearer's prescription data and the frame selected by the wearer. There are no particular restrictions imposed with respect to the method through which the input data in FIG. 3 may be obtained.

Once the input data are entered, the operation proceeds to step S1003.

In step S1003, the outside world model construction unit 11 constructs an outside world model based upon the outside world description data having been input in step S1001. The outside world model construction unit 11 disposes geometric objects at their respective positions and sets lighting and a gazing point within a virtual space in which a position is specified with three-dimensional coordinate values.

Figure 4:
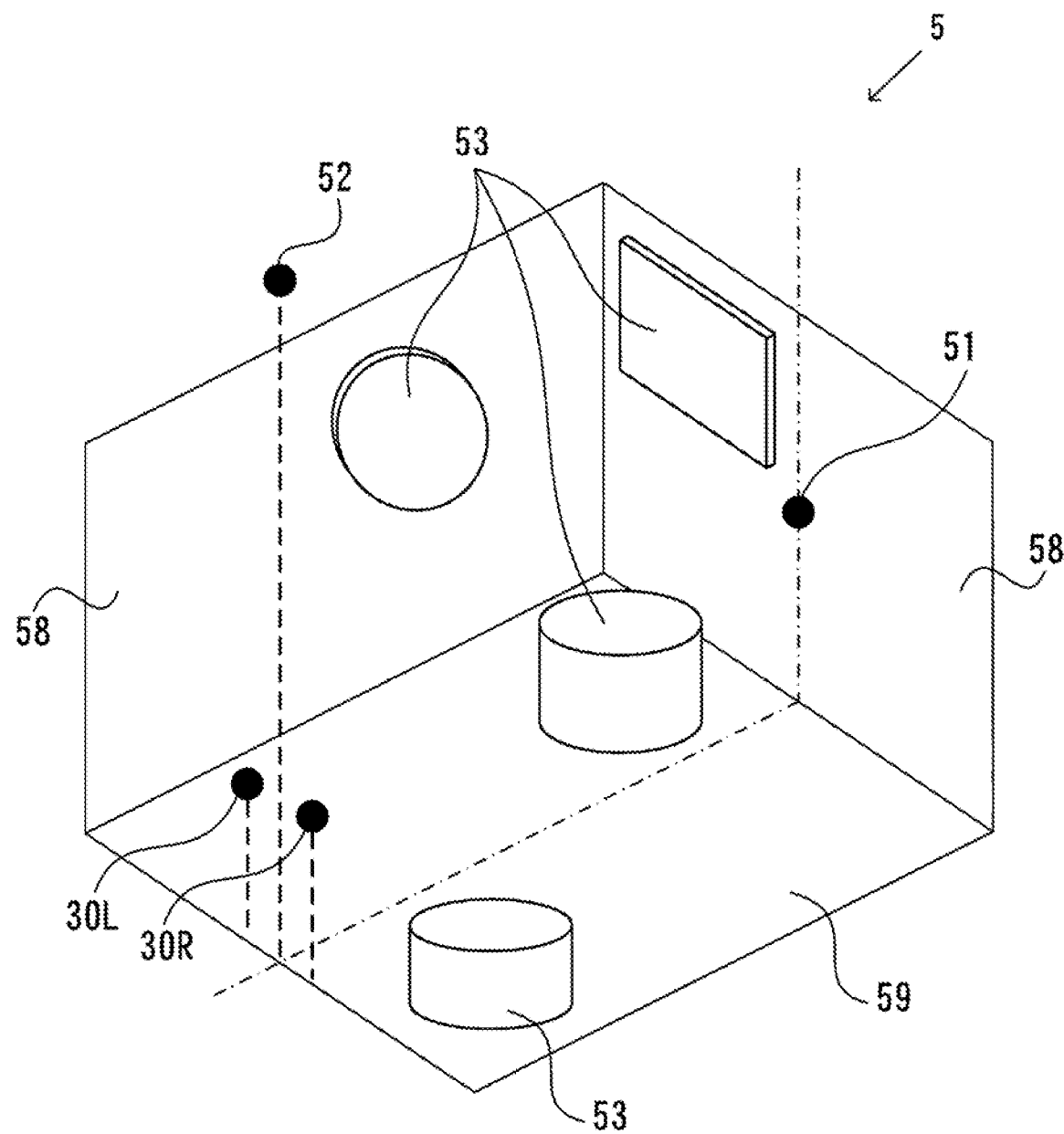
FIG. 4 is an illustration of a structure of an outside world model used in the image creation device in the embodiment

FIG. 4 presents an example of an outside world model. In order to facilitate an explanation, the illustration includes a left eyeball model 30L and a right eyeball model 30R set in the outside world model. An outside world model 5 includes a gazing point 51, lighting 52, objects 53, walls 58 and a floor 59. The gazing point 51 indicates a position at which the eyeball models 30L and 30R virtually view. The lighting 52 illuminates a target scene expressed with the outside world model. The objects 53 are each a geometric object or a composite object composed by combining a plurality of geometric objects, and they represent interior articles such as a painting, an ornament, a desk, a chair and the like in the target scene. The walls 58 and the floor 59 may be expressed with sets of predetermined data or they may be set based upon input data.

It is to be noted that an article used for visual acuity measurement, such as an eye chart, may be disposed as an object 53. Such an object can be used for virtual reference when checking visual acuity. In the outside world model 5, either the position at the center of the floor 59 or a position within a central area of the floor 59 may be set as the origin point in the coordinate system, or any other position may be set as the origin point.

Once the outside world model is constructed, the operation proceeds to step S1005.

In step S1005, the eyeball model construction unit 12 constructs eyeball models based upon the eyeball description data having been input in step S1001.

It is to be noted that while an explanation is given by assuming that the processing in each of steps S1005 through S1009 is executed for both eyes before proceeding to subsequent steps, the processing in step S1005 through step S1009 may be first executed for one eye and then the processing in step S1005 through step S1009 may be executed for the other eye.

Figure 5:
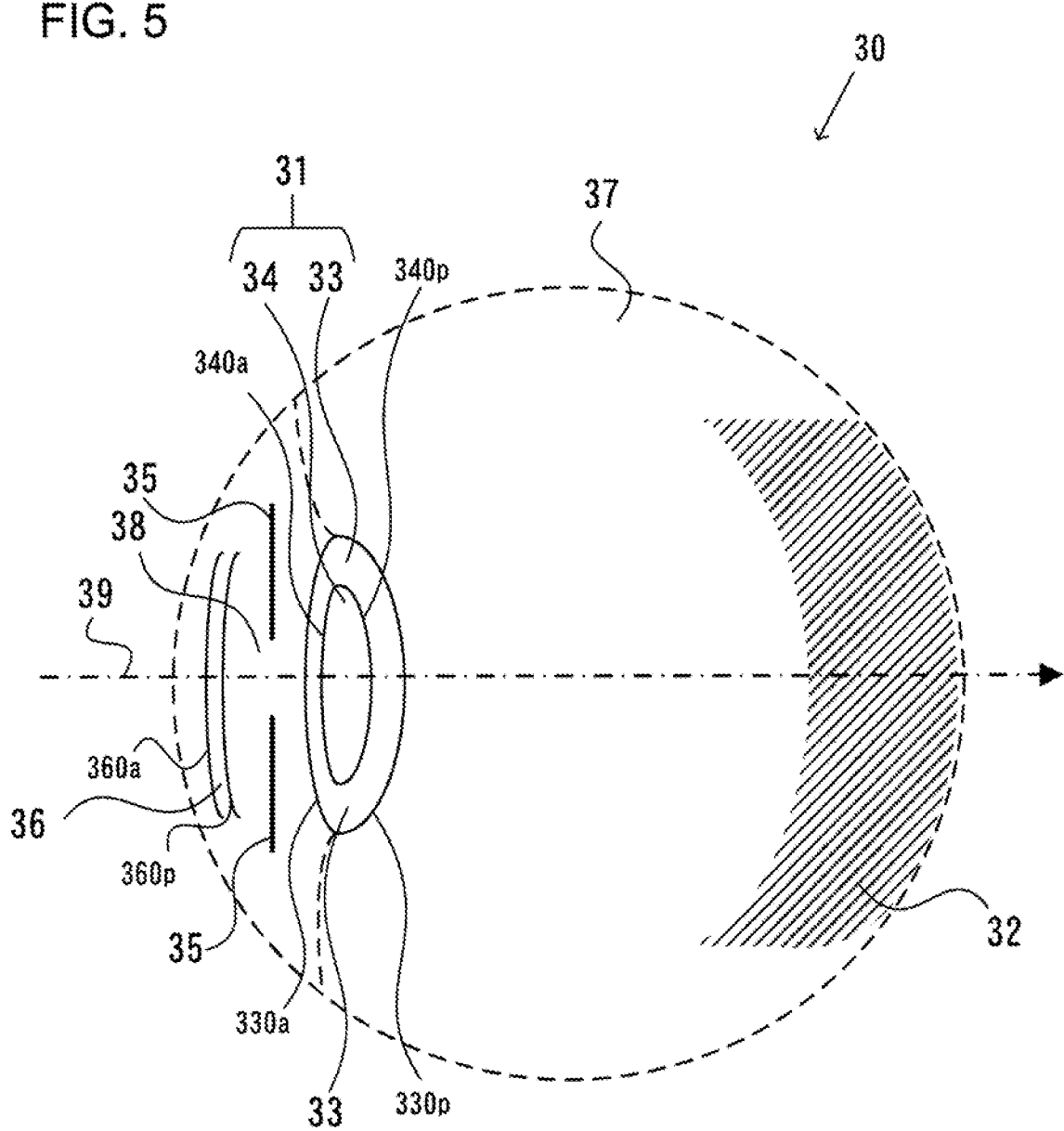
FIG. 5 is an illustration of an eyeball model used in the image creation device in the embodiment

FIG. 5 presents an example of an eyeball model. An eyeball model 30 includes a crystalline lens 31, a retina 32, a pupil 35, a cornea 36, vitreous humor 37, and an anterior chamber 38. The crystalline lens 31 includes a crystalline lens edge 33 and a crystalline lens core 34. The crystalline lens edge 33 includes a crystalline lens posterior surface 330$p$ and a crystalline lens anterior surface 330$a$. The crystalline lens core 34 includes a crystalline lens core posterior surface 340$p$ and a crystalline lens core anterior surface 340$a$. The cornea 36 includes a cornea posterior surface 360$p$ and a cornea anterior surface 360$a$. In the eyeball model 30, an optical axis 39 of an eye optical system, which includes the crystalline lens 31, the retina 32, the pupil 35 and the cornea 36, is defined. Since the eyeball model 30 is expressed with three-dimensional profile structure data, the optical axis 39 can be decentered or tilted.

The retina 32 is shown as the hatched area. A retina projection area that is not shown in the figure is defined for the retina 32 in the input data, and light entering the retina projection range is the subject of ray tracing, as will be explained later. At the crystalline lens in an actual eyeball, the refractive index at a central area and the refractive index in a peripheral area are different from each other and accordingly, the crystalline lens in the eyeball model 30 is modeled so as to achieve characteristics such as refractive indices that are optically equivalent for the two areas, i.e., the crystalline lens edge 33 and the crystalline lens core 34, assuming different refractive indices.

The pupil 35 is modeled so as to allow light to be transmitted through the opening at the center thereof by simulating its optical characteristics as an aperture. While the cornea anterior surface 360$a$ is the area where light having departed an object located outside the body, enters, the light is refracted over the entire cornea 36. The vitreous humor 37 is a medium constituting the optical path between the crystalline lens posterior surface 330$p$ and the retina, whereas the anterior chamber 38 is a medium constituting the optical path extending between the crystalline lens anterior surface 330$a$ and the cornea posterior surface 360$p$.

In the eyeball model 30, the positions of the various optical elements constituting the eye optical system are defined. In addition, refractive index values are defined for the cornea 36, the vitreous humor 37, the anterior chamber 38, the crystalline lens edge 33 and the crystalline lens core 34. Furthermore, radii of curvature and the like are individually defined in correspondence to the cornea anterior surface 360$a$, the cornea posterior surface 360$p$, the crystalline lens anterior surface 330$a$, the crystalline lens posterior surface 330$p$, the crystalline lens core anterior surface 340$a$ and the crystalline lens core posterior surface 340$p$.

It is to be noted that the eyeball model design can be optimized by, for instance, designing the crystalline lens 31 in smaller sectors, and the orientations of the various components, reference positions and the like in the eyeball model may be adjusted.

In addition, in order to simulate the accommodation function of the wearer, the eyeball model construction unit 12 constructs an eyeball model 30 in which the crystalline lens edge 33 and the crystalline lens core 34 are changed to have different thicknesses, as well.

Figure 6A:
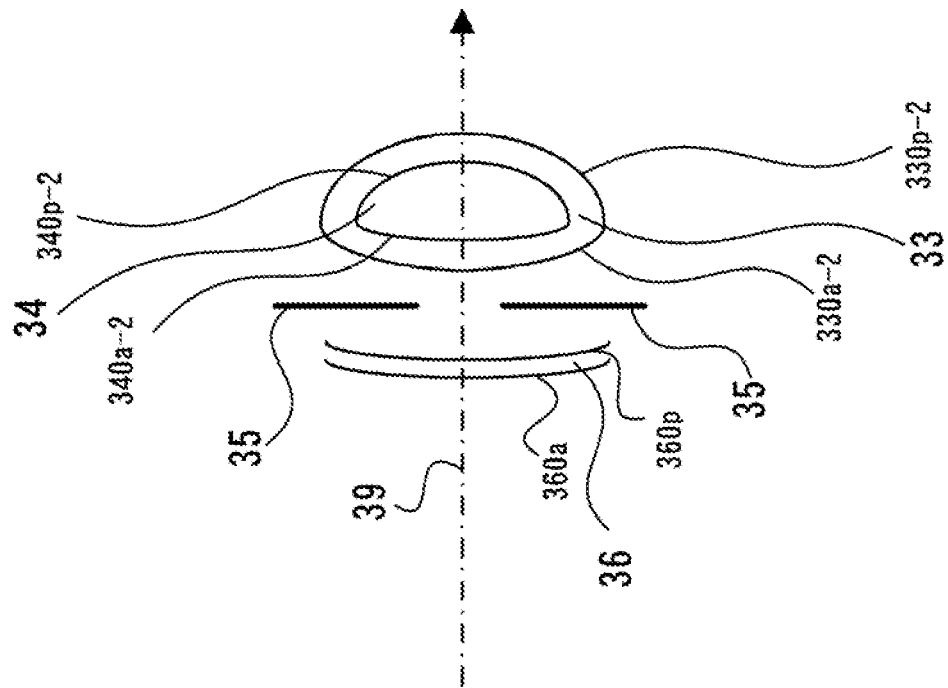
FIG. 6A is an illustration showing how a change occurs in the eyeball model in the image creation device achieved in the embodiment, showing the structure of the eyeball model in an eyeball lens non-contracted state
Figure 6B:
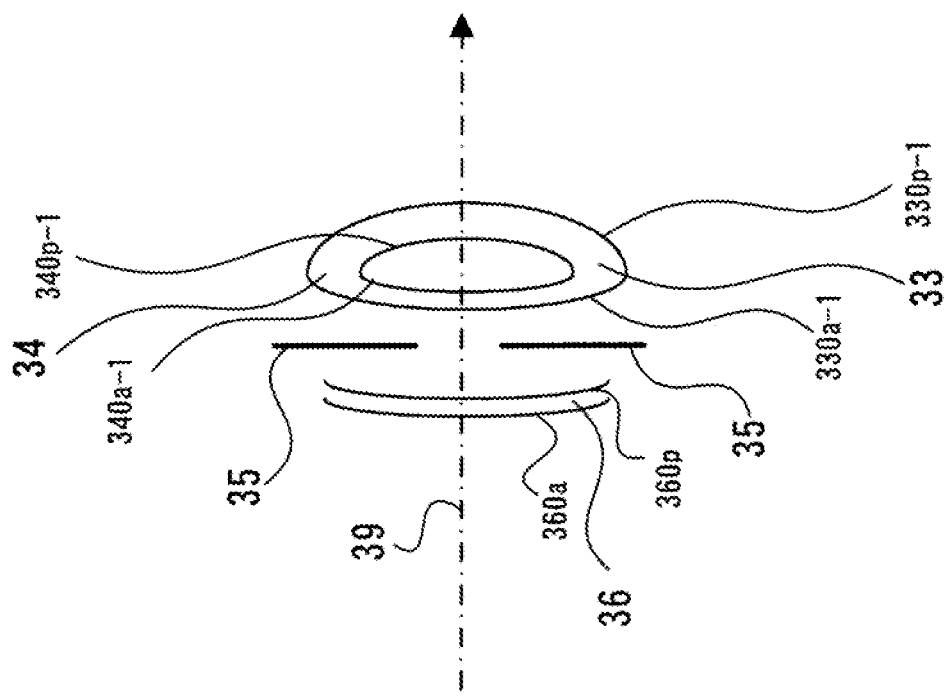
FIG. 6B is an illustration showing how a change occurs in the eyeball model in the image creation device achieved in the embodiment, showing the structure of the eyeball model in an eyeball lens contracted state

FIGS. 6A and 6B presents illustrations of a lens system that includes the crystalline lens edge 33, the crystalline lens core 34, the pupil 35 and the cornea 36 in the eyeball model 30 in FIG. 5. In FIGS. 6A and 6B, the same reference numerals are assigned to elements corresponding to those in FIG. 5 so as to preclude the necessity for a repeated explanation thereof. The crystalline lens edge 33 and the crystalline lens core 34 in FIG. 6A are in a pre-contraction state (non-contracted state), with smaller distances setting apart a crystalline lens core anterior surface 340$a$-1 from a crystalline lens core posterior surface 340$p$-1 and a crystalline lens anterior surface 330$a$-1 from a crystalline lens posterior surface 330$p$-1, compared to the corresponding distances in a contracted state in FIG. 6B, which will be explained later.

In FIG. 6B, a change occurring in the lens system in FIG. 6A as a result of a change made by the wearer in the accommodation is simulated. The thicknesses of the crystalline lens edge 33 and the crystalline lens core 34, measured along the optical axis, have increased, and the distance between a crystalline lens anterior surface 330$a$-2 and a crystalline lens posterior surface 330$p$-2 and the distance between a crystalline lens core anterior surface 340$a$-2 and a crystalline lens core posterior surface 340$p$-2 have both increased. In addition, the absolute values representing the radii of curvature of the crystalline lens anterior surface 330$a$-2, the crystalline lens posterior surface 330$p$-2, the crystalline lens core anterior surface 340$a$-2 and the crystalline lens core posterior surface 340$p$-2 have decreased. In order to create a moving image, the eyeball model construction unit 12 creates a plurality of eyeball models 30 corresponding to a plurality of stages over which the positions and the radii of curvature of the crystalline lens anterior surface 330$a$, the crystalline lens posterior surface 330$p$, the crystalline lens core anterior surface 340$a$ and the crystalline lens core posterior surface 340$p$ change from those in the state shown in FIG. 6A to those shown in FIG. 6B. Once the eyeball models 30 are constructed, the operation proceeds to step S1007.

It is to be noted that a plurality of eyeball models 30 may be constructed by altering parameters related to the cornea 36, the cornea anterior surface 360$a$, the cornea posterior surface 360$p$, the pupil 35 and any other optical elements. In addition, a plurality of eyeball models 30 may be constructed in correspondence to changes in the environment such as lighting in the outside world model 5. For instance, the size of the opening at the pupil 35 may be altered based upon the intensity of light ascertained through feedback of the intensity of light reaching the retina, determined through ray tracing, which will be explained later. In addition, an eyeball model 30 may be defined by determining change quantities representing extents of change for the crystalline lens edge 33 and the crystalline lens core 34 based upon the accommodation ability of the particular wearer.

In step S1007, the eyeglass lens model construction unit 13 constructs eyeglass lens models based upon the eyeglass lens description data having been input in step S1001. The eyeglass lens model construction unit 13 constructs three-dimensional models for eyeglass lenses based upon the eyeglass lens external shape information, the eyeglass lens central thickness and the surface shape data indicating the contours of the anterior and posterior surfaces of each eyeglass lens located on the object side and the eyeball side and the contour of the eyeglass lens surface in the peripheral areas. The surface shape data are expressed in a spline function and thus, an eyeglass lens model assuming any shape, including a progressive-power lens shape, can be created. Once the eyeglass lens models are constructed, the operation proceeds to step S1009.

It is to be noted that no particular restrictions are imposed with regard to the method of eyeglass lens model construction, as long as three-dimensional eyeglass lens models can be constructed, and they may be constructed by using shape data available at the retail store.

In step S1009, the ray tracing unit 15 in the retina image creation unit 14 calculates the optical path, the intensity, the wavelength distribution and the like of light from the outside world model 5 that enters each retina 32 at a specific position among various positions through ray tracing. In the first stage of ray tracing for light traveling inside each eyeball model 30, the ray tracing unit 15 traces a ray of light entering each position within the retina projection range of the retina 32 along a direction opposite from the light advancing direction so as to calculate the position and the direction of light entry at the cornea anterior surface 360a.

Figure 7:
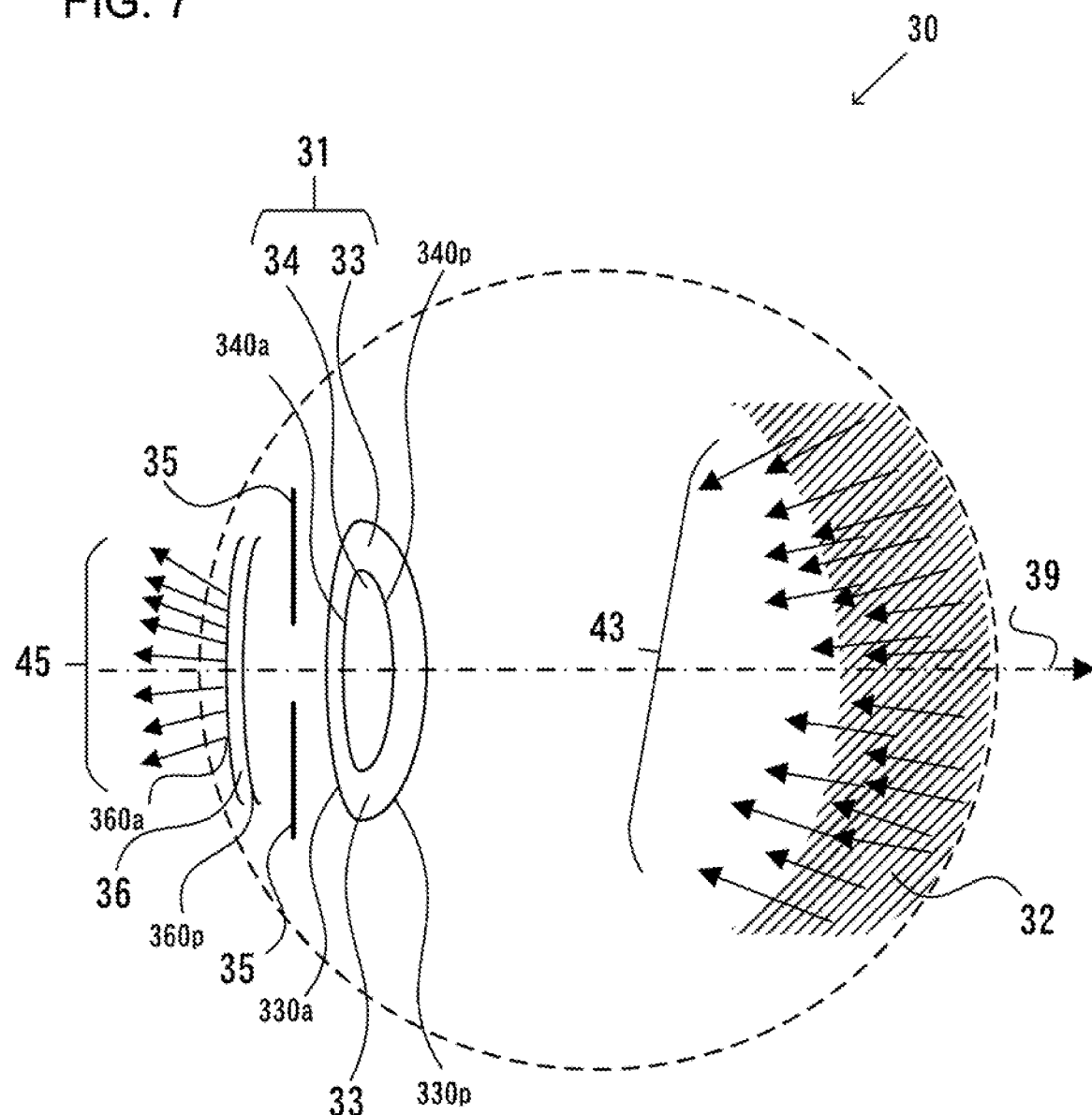
FIG. 7 is a conceptual diagram illustrating how rays of light are traced in the image creation device in the embodiment

FIG. 7 schematically illustrates how the ray tracing unit 15 traces rays of light inside the eyeball model 30. In the example presented in FIG. 7, the retina projection range is set over a range of the spherical surface of the retina defined by a 90° longitude and a 90° latitude. Ray tracing may be executed by tracing light 43 departing each position taken within the retina projection range at the retina 32 and calculating the position and the advancing direction of corresponding light 45 departing the cornea anterior surface 360a. By reversing the advancing direction of the light 45 departing the cornea anterior surface 360a, the position and the direction of light entry at the cornea anterior surface 360a corresponding to the particular position at the retina 32 can be calculated.

In the second stage of ray tracing for tracing light in the outside world model 5, the ray tracing unit 15 calculates an intersecting point at which the ray of light intersects an outside world object by tracing the ray of light along the reverse direction based upon the position and the advancing direction of the light entering the cornea anterior surface 360a having been ascertained through the first stage, traces reflected•transmitted light and executes calculation with respect to the lighting. For instance, the ray tracing unit 15 is able to execute calculation to determine, based upon the position and the advancing direction of light entering the cornea anterior surface 360a, a specific point on the object in the outside world model at which the particular light has been scattered and is also able to calculate the intensity, the wavelength and the like of the light based upon the light cast onto the object point by referencing information indicating the reflectance and the like at the particular object point.

Based upon the intensity and the wavelength of the light traveling from the particular object point in the outside world model thus ascertained, the ray tracing unit 15 calculates the luminance, represented with RGB values or the like, at each point in the retina 32. Luminance data indicating luminance at various points in the retina 32 thus obtained constitute a retina image.

Figure 8:
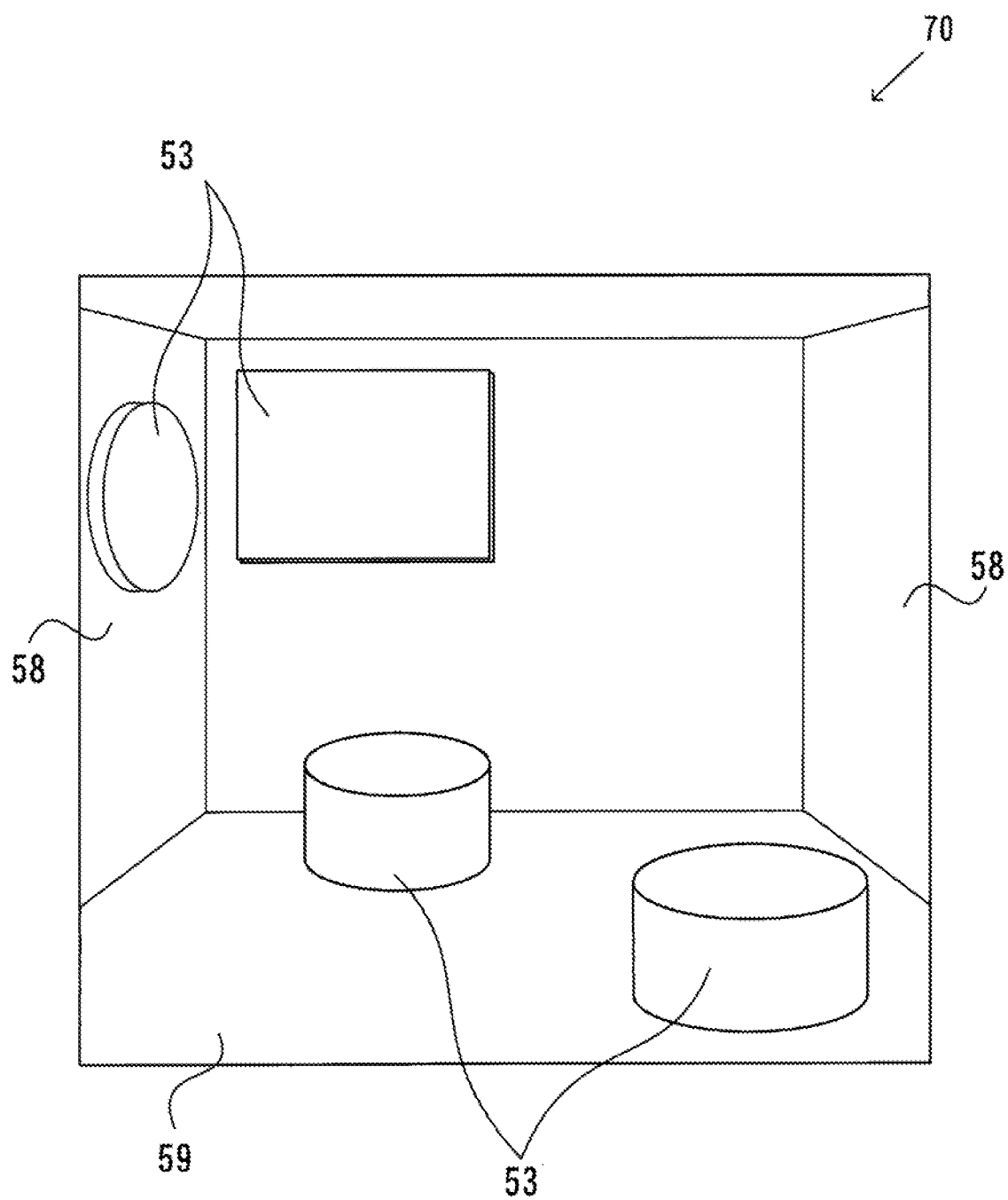
FIG. 8 is an illustration presenting an example of a retina image that may be created in the image creation device in the embodiment

FIG. 8 presents an example of a retina image. The retina image in FIG. 8 is an image of the outside world model 5 in FIG. 4 projected onto the right eyeball model 30R as the outside world model 5 is virtually viewed at the gazing point 51 (see FIG. 4) with the right eyeball model 30R. FIG. 8 shows that the walls 58, the floor 59 and the objects 53 are projected in the retina image 70.

The retina image 70 is created by assigning points in the retina 32, which has a curved surface, to two-dimensional coordinate points. The retina image creation unit 14 approximates the shape of the retina 32 as part of a spherical retina surface, and maps the luminance levels at various points in the retina 32 indicated in the luminance data obtained by the ray tracing unit 15 through calculation, by setting latitudinal/longitudinal angles on the retina sphere each in correspondence to a coordinate position on the two-dimensional plane. The retina image creation unit 14 may map the luminance data over a range defined by longitudes $\theta 0$ through $\theta 1$ and latitudes $\Phi 0$ through $\Phi 1$ onto a retina image 70 made up with Nh×Nv pixels. Nh represents the number of pixels present along the horizontal direction, whereas Nv represents the number of pixels present along the vertical direction. In addition, Sh and Sv, in Sh×Sv that represents the size of each pixel, are calculated as; Sh=($\theta 1-\theta 0$)/Nh and Sv=($\Phi 1-\Phi 0$)/Nv. A position corresponding to each pixel may be set by calculating it as, for instance, $\theta=\theta 0+(i+\frac{1}{2})\cdot Sh$, and $\Phi=\Phi 0+(j+\frac{1}{2})\cdot Sv$, with i and j satisfying conditions expressed as; $0 \leq i < Nh$ and $0 \leq j < Nv$. Once retina images 70 are constructed for the two eyes, the operation proceeds to step S1011.

It is to be noted that while the luminance data are two dimensionally mapped in correspondence to the angles on the retina sphere, data in a three-dimensional spherical coordinate system (r, $\theta$, $\Phi$) may be converted to data in a three-dimensional rectangular coordinate system (x, y, z) and then the data may be directly projected onto any plane such as an XZ plane. For instance, the retina image creation unit 14 may set the origin point of the coordinate system at the intersecting point at which the optical axis 39 in the eyeball model 30 intersects the retina 32 and may project the luminance data at the various points on the retina 32 onto a plane passing through the origin point and ranging perpendicular to the optical axis. It is to be noted that calculation may be executed when converting the data in the three-dimensional spherical coordinate system (r, $\theta$, $\Phi$) to those in a three-dimensional rectangular coordinate system (x, y, z) by using a conversion formula of the known art. No particular restrictions are imposed with regard to the coordinate system setting method, e.g., the method for setting the origin point, as long as a desired conversion can be achieved.

In step S1011, the corresponding point calculation unit 17 calculates corresponding points in the left and right retina images 70. The term "corresponding points" is used in relation to pixels that correspond to a given object point in the outside world model 5, to refer to positions in the left and right retina images 70 at which the particular object point is projected or pixels corresponding to these positions.

Figure 9A:
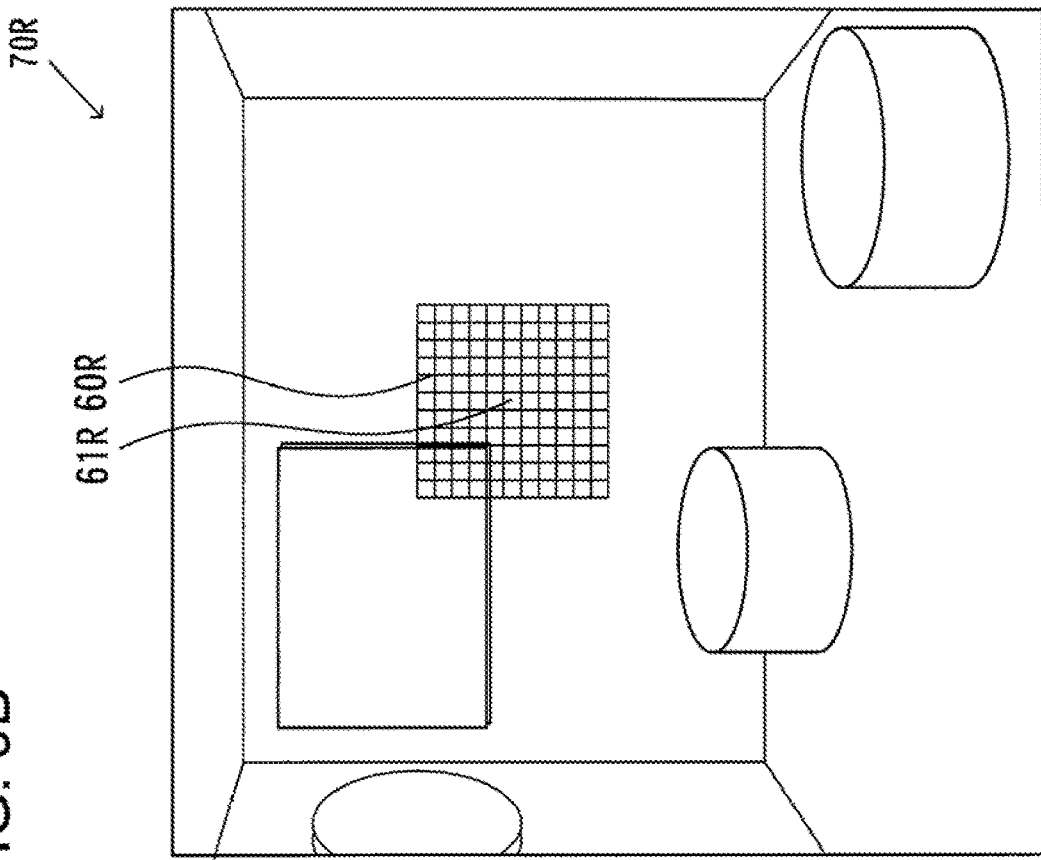
FIG. 9A is a conceptual diagram illustrating how corresponding points in retina images for two eyes are calculated in the image creation device in the embodiment, presenting an example of a left-eye retina image
Figure 9B:
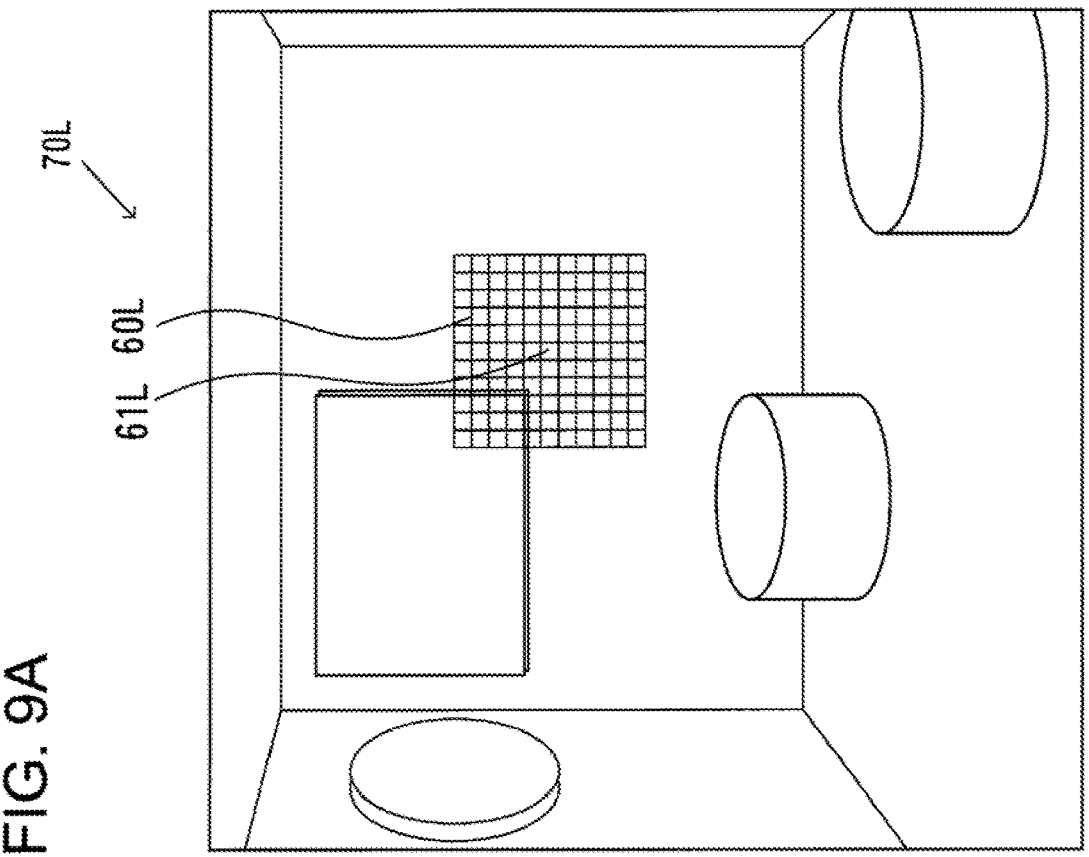
FIG. 9B is a conceptual diagram illustrating how corresponding points in retina images for two eyes are calculated in the image creation device in the embodiment, presenting an example of a right-eye retina image

FIGS. 9A and 9B illustrates how corresponding points are calculated. FIG. 9A includes a template 60L indicating a calculation range set for the corresponding point calculation, added in the retina image 70L corresponding to the left eyeball model 30L in FIG. 4. FIG. 9B includes a template 60R indicating a calculation range set for the corresponding point calculation, added in the retina image 70R corresponding to the right eyeball model 30R in FIG. 4. The template 60L and the template 60R in the embodiment are each made up with pixels present in an 11×11 square range centered on the corresponding pixel.

It is to be noted that an optimal adjustment may be made when setting a template in correspondence to a target pixel. For instance, a square template may be set by adjusting its size to a 3×3 pixel area, a 5×5 pixel area, a 17×17 pixel area or the like.

The corresponding point calculation unit 17 calculates a degree of similarity between the luminance values at pixels included in the template 60L corresponding to a given pixel 61L in the left-eye retina image 70L, and the luminance values at pixels included in a template 60R corresponding to a given pixel 61R in the right-eye retina image 70R. The corresponding point calculation unit 17 in the embodiment calculates the degree of similarity between the luminance values at a plurality of pixels included in the template 60L and a plurality of pixels included in the template 60R based upon correlation coefficients. For instance, it may set the origin point of a coordinate system in each of the left and right retina images 70 at a position corresponding to the intersecting point at which the optical axis 39 of the eyeball model 30 intersects the retina 32, assume an X axis and a Y axis respectively along the lateral direction and the longitudinal direction in the image and specify each pixel within the template as a local coordinate point (xi, yj). When a luminance value corresponding to the left eye and a luminance value corresponding to the right eye are respectively expressed as a local coordinate function, fl(xi, yj) and as a local coordinate function fr(xi, yj), a correlation coefficient Dcorr between a template 60L and a template 60R, the central pixels of which are offset by (dx, dy), can be calculated as expressed in (1) below.

[Math. 1]

$$D_{corr} = \frac{\sum_{i=0}^{n}\sum_{j=0}^{n}(f_l(x_i, y_j) - \overline{f_l})(f_r(x_i + dx, y_j + dy) - \overline{f_r})}{\sqrt{\sum_{i=0}^{n}\sum_{j=0}^{n}(f_l(x_i, y_j) - \overline{f_l})^2}\sqrt{\sum_{i=0}^{n}\sum_{j=0}^{n}(f_r(x_i + dx, y_j + dy) - \overline{f_r})^2}} \quad (1)$$

fl and fr with macrons each represent the average of the luminance values in the entire template, which is calculated as expressed in (2) below.

[Math. 2]

$$\overline{f_l} = \frac{\sum_{i=0}^{n}\sum_{j=0}^{n}f_l(x_i, y_j)}{n^2} \quad (2)$$

$$\overline{f_r} = \frac{\sum_{i=0}^{n}\sum_{j=0}^{n}f_r(x_i + dx, y_j + dy)}{n^2}$$

The corresponding point calculation unit 17 calculates correlation coefficients with respect to luminance values in the template centered on a given pixel 61L in the left-eye retina image 70L and luminance values in the template offset by dx and dy along the X axis and the Y axis from the pixel taking the position corresponding to the pixel 61L in the right-eye retina image 70R. The corresponding point calculation unit 17 alters dx and dy each over a range of zero pixels through several pixels and determines a template achieving a high degree of similarity, i.e., with the highest correlation coefficient and the pixel at the center of the template. The central pixel thus determined is paired up with the pixel 61L as its corresponding point 61R.

It is to be noted that the differences between corresponding pixels in two templates may be determined, the degree of similarity may be calculated as the sum of squares of the differences and corresponding points may be calculated by determining templates achieving the least sum of squares of differences, instead of calculating corresponding points based upon correlation coefficients. In addition, the degree of similarity may be calculated based upon luminance represented by any of R, G and B values or based upon a luminance signal Y or the like calculated based upon RGB data. Furthermore, while a corresponding point in a right eye for a given pixel 61L in a left eye is searched in the example explained above, a corresponding point in the left eye may be searched for a given pixel in the right eye, instead.

Once the corresponding point calculation unit 17 calculates corresponding points of respective pixels in the left and right retina images 70, it creates a disparity distribution by mapping disparities, each represented by the numbers of pixels by which a pair of corresponding points in the retina images 70 for the two eyes are offset from each other along the X direction and the Y direction, in correspondence to the retina images 70, or creates a disparity display image indicating the disparity distribution. Once the corresponding point calculation and the creation of a disparity distribution or the like are completed, the operation proceeds to step S1013.

In step S1013, the binocular view image creation unit 18 creates a binocular view image 71 by combining the left and right retina image 70L, 70R.

Figure 10:
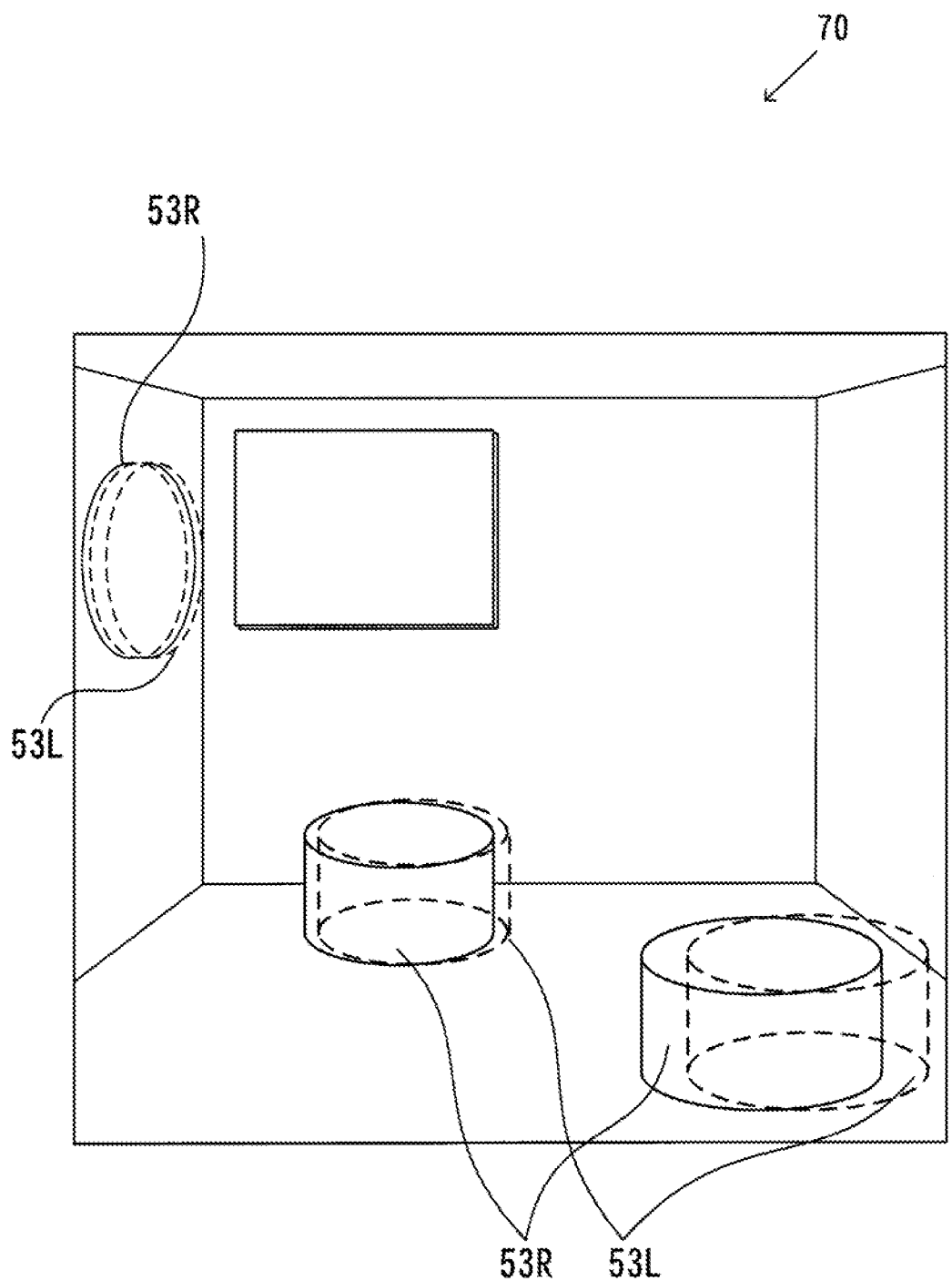
FIG. 10 is a conceptual diagram illustrating how a binocular view image may be constructed in the image creation device in the embodiment

FIG. 10 shows the left and right retina images 70 superimposed one upon another without processing them first. Due to disparity, if the left and right retina images 70 are combined without first processing the retina images 70, the corresponding points do not align and thus, a clear composite image cannot be created. FIG. 10 schematically illustrates offsets by indicating objects 53L in the left-eye retina image 70L with dotted lines and indicating objects 53R in the right-eye retina image 70R with solid lines. The binocular view image creation unit 18 combines the left and right images by locally offsetting them based upon disparity information corresponding to the individual pixels and a correction parameter used to correct the disparities. An optimal correction parameter may be set based upon experience. Such a correction parameter makes it possible to adjust the rate concerning ratio of fusion, i.e., the ratio of the right-side luminance to the left-side luminance, with which the images are combined, or the ratio with which the left image and the right image are offset relative to each other, based upon, for instance, the degree of dominance of one eye.

Figure 11:
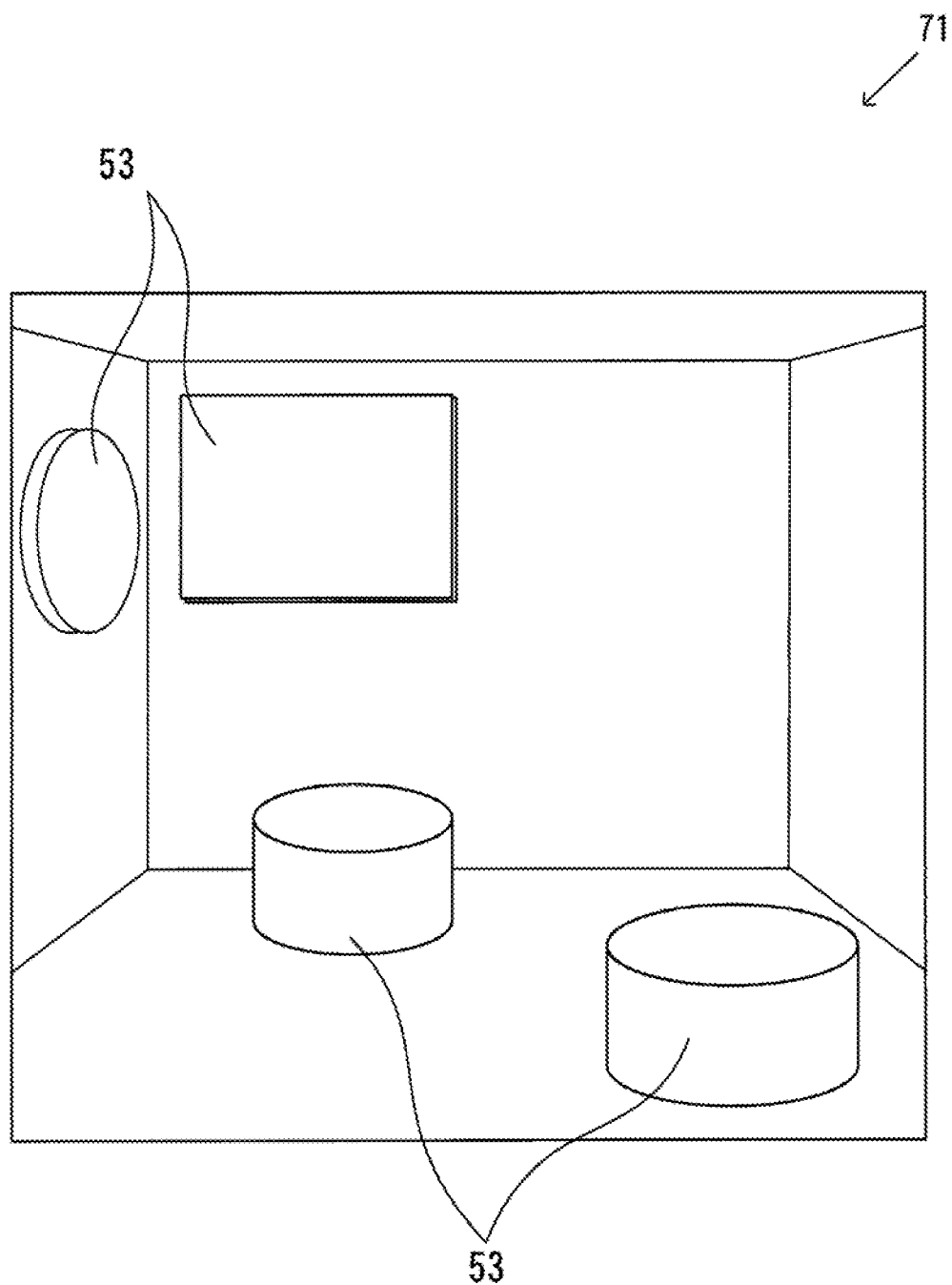
FIG. 11 is an illustration presenting an example of a binocular view image that may be created in the image creation device in the embodiment

FIG. 11 shows a binocular view image 71 obtained by combining the retina images 70. A clear image is obtained, unlike the image that is shown in FIG. 10 and created by superimposing the left and right retina images 70.

Once the binocular view image 71 is created, the operation proceeds to step S1015.

In the step S1015, the binocular view image creation unit 18 processes the binocular view image 71 having been obtained through step S1013 so as to create a display image. Once the processing in step S1015 is completed, the operation proceeds to step S1017.

It is to be noted that the binocular view image creation unit 18 may provide the moving image creation unit 18 with a plurality of binocular view images 71 obtained by repeatedly executing the processing in step S1003 through step S1013, so as to enable the moving image creation unit 19 to create a moving image. The moving image creation unit 19 creates a moving image structured so as to successively display a plurality of binocular view images 71 obtained by altering parameters in the input data or the like. For instance, it may create a moving image that includes changes occurring in the crystalline lens edge 33 and the crystalline lens core 34 during a time period between the state shown in FIG. 6A and the state shown in FIG. 6B based upon binocular view images 71 created in correspondence to eyeball models 30 in a plurality of different stages between the two states.

The moving image may be created by altering a given parameter in the eyeball models 30 along the time axis. As an alternative, a moving image may express changes occurring in the retina images 70 or the like as a result of virtual eye movement occurring, for example, as the direction of the line of sight changes.

In step S1017, the display unit 21 brings up on display the retina images 70, the binocular view image 71, the disparity display image, the moving image or the like having been created. Once the retina images 70 or the like having been created are brought up on display, the operation proceeds to step S1019.

In step S1019, the control unit 10 makes a decision as to whether or not to display retina images 70 or the like by switching to different eyeglass lenses. If the wearer or the sales clerk at the eyeglass store enters an instruction for creating retina images 70 and the like again by switching to different eyeglass lenses upon checking the retina images 70, the binocular view image 71, the disparity display image, the moving image and the like brought up on display at the display unit 21, the control unit 10 makes an affirmative decision in step S1019, and the operation returns to step S1007. Otherwise, a negative decision is made in step S1019 and the operation proceeds to step S1021.

It is to be noted that if the operation returns to step S1007, the control unit 10 may issue a redesign instruction to a designing device 93 (see FIG. 12) as needed. The designing device 93 may design eyeglass lenses based upon the shapes of the eyeglass lenses having been used when creating the retina images 70 and the like, the correction parameter having been used when creating the binocular view image 71, the disparity distribution or the like.

In step S1021, the control unit 10 transmits to the designing device 93 (see FIG. 12) a processing instruction with regard to the eyeglass lenses used in the creation of the retina images 70 together with any information required for eyeglass lens processing. Once the processing instruction is transmitted, the operation proceeds to step S1023.

Figure 12:
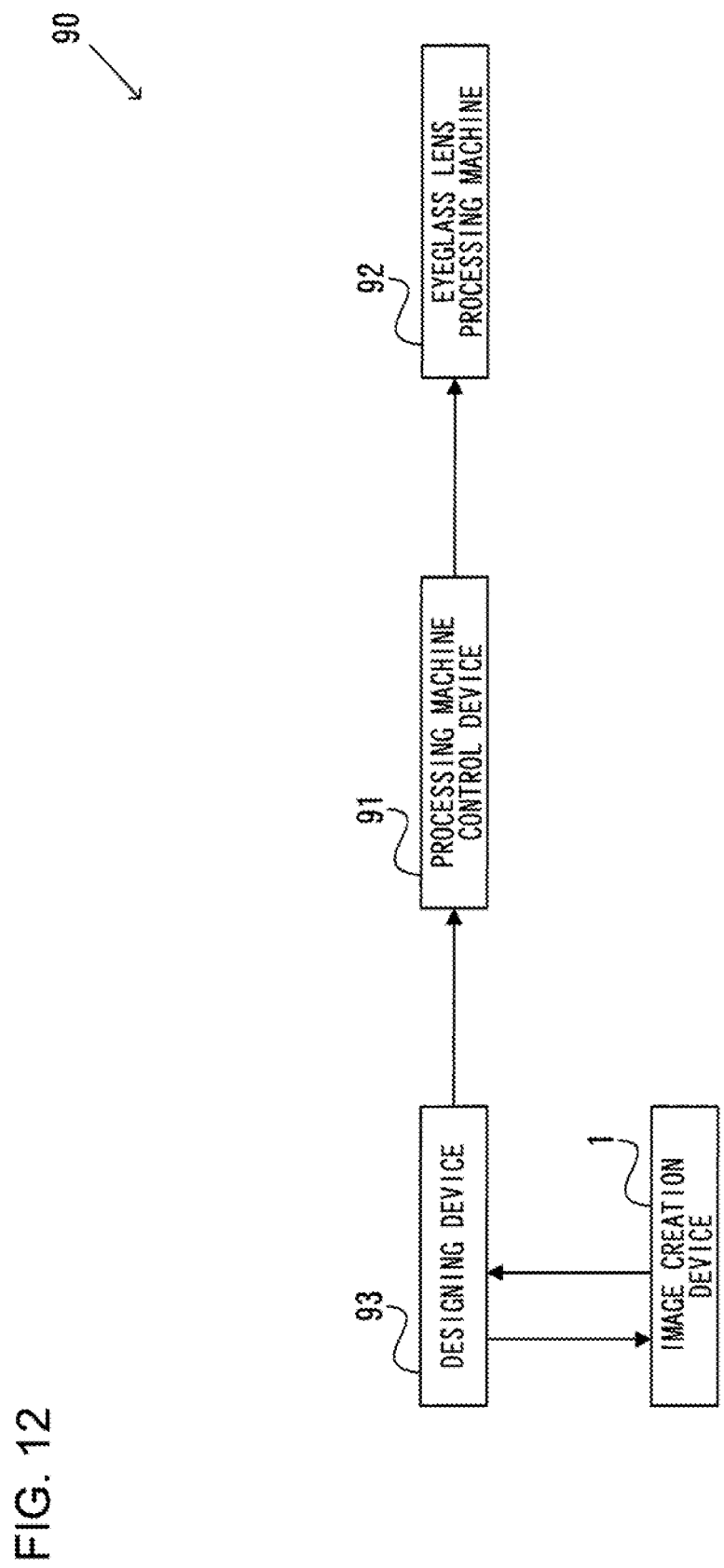
FIG. 12 is a conceptual diagram showing a configuration of an eyeglass lens manufacturing system that includes the image creation device in the embodiment

FIG. 12 shows an eyeglass lens manufacturing system 90 that manufactures the eyeglass lenses having been used by the image creation device in the embodiment for purposes of creating the retina images 70. The eyeglass lens manufacturing system 90 comprises the image creation device 1, a processing machine control device 90, an eyeglass lens processing machine 92 and the designing device 93. The arrows in FIG. 12 indicate how the data used in the eyeglass lens production flow.

In step S1023, the eyeglass lens processing machine 92 manufactures eyeglass lenses, the processing instruction for which has been transmitted in step S1021. The designing device 93 transmits eyeglass lens design data, having been transmitted to the image creation device 1 as, for instance, part of the input data, to the processing machine control device 91, and under control executed by the processing machine control device 91, the eyeglass lens processing machine 92 manufactures the eyeglass lenses.

The following advantages and operations are achieved through the embodiment described above.

(1) The image creation device 1 in the embodiment includes a retina image creation unit 14 that creates retina images 70 of an outside world model 5 that is virtually viewed by a wearer through eyeglass lenses, projected onto the retinas of the two eyes of the wearer, based upon outside world description data pertaining to the positional arrangement with which objects 53 are set in the outside world model 5, the shapes of the objects 53 and the optical characteristics such as the reflectance of the objects 53, eyeglass lens description data with respect to the positions taken by eyeglass lenses, their shapes and the optical characteristics such as the refractive indices of the eyeglass lenses, and eyeball description data with respect to the positions and the shapes of the eyes of the wearer virtually viewing the outside world model 5 through the eyeglass lenses and the optical characteristics such as the refractive indices of the wearer's eyes. Thus, images that would be viewed in various actual situations can be simulated in correspondence to the structures of the eyeballs of the wearer virtually wearing the eyeglass lenses, the scene, the particulars of the eyeglass lenses and the like.

(2) The image creation device 1 in the embodiment includes a corresponding point calculation unit 17 that calculates corresponding points in the retina images 70 for the two eyes, which correspond to a given position in the outside world model 5, and calculates the binocular disparity in correspondence to the position based upon the corresponding points having been calculated. As a result, a disparity that would occur in an actual situation can be simulated by assuming that the wearer is wearing eyeglasses.

(3) The image creation device 1 in the embodiment calculates the corresponding points based upon the correlation coefficients Dcorr or the differences with respect to the luminance values at the individual pixels included in a template 60L made up with a plurality of pixels, which is set in the left-eye retina image 70L, and the luminance values at the individual pixels included in a template 60R made up with a plurality of pixels, which is set in the right-eye retina image 70R. Through this process, corresponding points can be directly detected by comparing the two retina images 70 with each other.

(4) The binocular view image creation unit 18 in the image creation device 1 in the embodiment creates a binocular view image 71 by using the retina images 70 for the two eyes based upon the binocular disparity and a correction parameter indicating a degree to which the left and right image components are to be offset, the ratio of fusion or the like. As a result, a virtual image for binocular view corresponding to an actual scene, can be produced by assuming that the wearer is wearing eyeglass lenses.

(5) The display unit 21 in the image creation device 1 in the embodiment displays a binocular disparity distribution in correspondence to the retina images 70. As a result, the binocular disparity that would manifest in an actual situation can be anticipated by hypothesizing that the wearer is wearing eyeglass lenses.

(6) The ray tracing unit 15 in the image creation device 1 in the embodiment calculates the direction along which and the position at which a ray of light entering a given position taken in the retina 32 of each of the two eyes enters the cornea anterior surface 360*a* of the eye, and calculates a path along which a ray of light having departed the outside world model 5 passes through the cornea anterior surface 360*a* and reaches each position at the retina 32, and the luminance at the pixel corresponding to each position at the retina 30. Through this process, the light from the outside world model 5 that reaches the retinas 32 can be traced in an optimal manner.

(7) The display unit 21 in the image creation device 1 in the embodiment brings up on display the retina images 70 or binocular view images 71 generated based upon retina images 70 corresponding to the two eyes as a moving image reflecting changes occurring in the eyeball description data. Thus, an image that would be viewed in an actual situation while parameters with respect to the eyeballs are altered, can be simulated in a user-friendly manner.

(8) The image creation device 1 in the embodiment calculates the shapes of the two eyes based upon the accommodation ability of the wearer and the diameters of the pupils of the wearer's eyes. Thus, the refractive power and the degree of aperture opening achieved in the ophthalmological optical system can be re-created in an optimal manner.

The following variations are also within the scope of the present invention, and may be adopted in combination with the embodiment described above.

Variation 1

The retina image creation unit 14 in the above embodiment may create a retina image 70 in conjunction with a corrective lens by taking into consideration an eyeball structure with ametropia. In such a case, a lens that optimally corrects ametropia can be provided based upon a retina image 70 or the like in the embodiment.

In this variation retina images 70, a binocular view image 71, a disparity distribution, a moving image and the like are created. In addition, the eyeglass lens model construction unit 13 constructs a virtual corrective lens model and outputs it to the retina image creation unit 14. The retina image creation unit 14 creates a retina image 70 based upon the corrective lens model. The virtual corrective lens model can be constructed based upon input data related to the wearer's prescription or a corrective lens entered via the input unit 8. Retina images 70, binocular view images 71, disparity distributions, moving images and the like corresponding to the states with and without the corrective lens, can be displayed in a format that enables comparison, e.g., simultaneously, by the display unit 21.

The retina image creation unit 14 in this variation creates retina images 70 projected onto the retinas 32 of the two eyes based upon data such as input data indicating the position, the shape and the optical characteristics of the virtual corrective lens. As a result, effects to be achieved through the corrective lens can be displayed in a user-friendly manner.

Variation 2

While the eyeball structures are expressed in the eyeball description data in the embodiment described above, eyeball description data may be instead generated through calculation executed based upon wearer prescription data. In such a case, eyeball models 30 can be constructed based upon the prescription data even if actual measurement of the eyeball structures of the wearer cannot be taken or data indicating the results of a direct measurement cannot be obtained.

Figure 13:
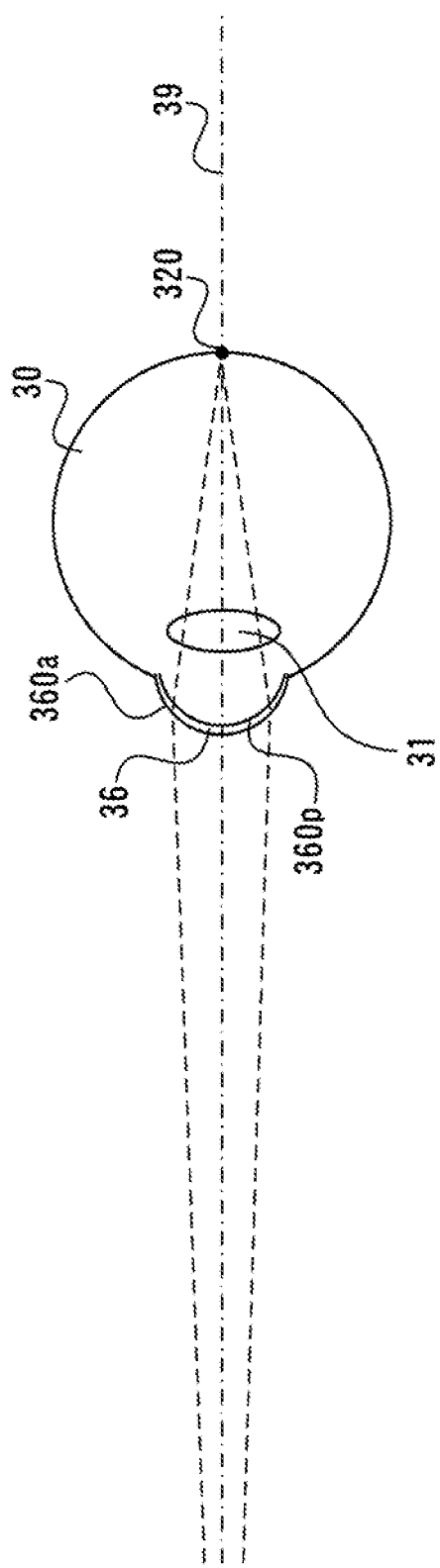
FIG. 13 is an illustration of a method of eyeball model construction adopted in an image creation device in an embodiment

FIG. 13 illustrates how eyeball description data may be generated through calculation based upon the wearer's prescription data. In this variation, parameters with respect to an eyeball structure, and more specifically, the curvatures or the radii of curvature of the cornea anterior surface 360*a* and the cornea posterior surface 360*p* are calculated by using an iterative algorithm based upon prescription data indicating the spherical power, the cylindrical power and the angle of the astigmatism axis. The illustration of an eyeglass lens model 30 in FIG. 13 includes a cornea 36, a crystalline lens 31, a retina central position 320, which is located on an optical axis 39 indicated with a one-point dotted line, and the like.

For an astigmatism-free wearer, the eyeball model construction unit 12 determines the curvatures of the cornea anterior surface 360*a* and the cornea posterior surface 360*p* so as to agree with the spherical power indicated in the prescription data. Namely, arbitrary values are set as the curvatures of the cornea anterior surface 360*a* and the cornea posterior surface 360*p*, and the refractive power at the ray wavefront at the position at which a ray, having departed the retina central position 320, passed through the pupil and exited the cornea, intersects a spherical surface set apart from the center of the eyeball rotation by 25 mm, is calculated through ray tracing executed based upon the arbitrary curvature values. The refractive power at the position at which the ray intersects the spherical surface set apart from the eyeball rotation center by 25 mm is compared with the prescription spherical power, and the curvature values having been used are selected as the curvatures of the cornea anterior surface 360*a* and the cornea posterior surface 360*p* if the absolute value of the difference between the calculated refractive power and the prescription spherical power is less than 0.02 diopters (hereafter will be notated as "D"). If, on the other hand, the absolute value of the difference between the refractive power at the intersecting position and the prescription spherical power is equal to or greater than 0.02 D, new values are set for the curvatures at the cornea anterior surface 360*a* and the cornea posterior surface 360*p* by increasing or decreasing the values based upon the value representing the difference between the refractive power at the intersecting position and the prescription spherical power, and ray tracing is executed again. For instance, a curvature may be tightened if the spherical power is +S degree, whereas the curvature may be flattened if the spherical power is −S. This procedure will be repeated until the difference between the refractive power at the intersecting point and the prescription spherical power becomes less than 0.02 D.

It is to be noted that while the reference value, based upon which a decision is made as to whether or not the current curvature settings for the cornea anterior surface 360a and the cornea posterior surface 360p that are to be selected, is 0.02 D in the example explained above, an optimal value such as 0.01 D, 0.03 D or the like may be set as the reference value. In addition, an optimal position should be set for the position at which the refractive power at the wavefront is calculated by, for instance, selecting a position within a range of 10 through 15 mm measured from the cornea along the optical axis. The same principle applies in the processing below executed for a wearer with astigmatism.

The cornea anterior surface 360a and the cornea posterior surface 360p are each considered to be a toric surface when the wearer has astigmatism. Such a toric surface is formed so as to include a surface achieving a smallest curvature, i.e., a base curvature, and a surface achieving a greatest curvature, i.e., a cross curvature, alternating each other every 90° around a predetermined axis, and is defined by the base curvature, the cross curvature and a direction along which the base curvature is assumed. The eyeball model construction unit 12 sets a base curvature, a cross curvature and a direction along which the base curvature is assumed, and calculates the base-direction refractive power, the cross-direction refractive power and the direction of the base refractive power at the ray wavefront at the position at which a ray of light having departed the cornea intersects a spherical surface set apart from the center of the eyeball rotation by 25 mm through ray tracing. The eyeball model construction unit 12 determines that the evaluation criteria are satisfied as long as the absolute value of the difference between the base-direction refractive power and the prescription spherical power and the absolute value representing the difference between a value obtained by subtracting the cross-direction refractive power from the base-direction refractive power and the prescription astigmatic power are each less than 0.02. The eyeball model construction unit 12 also judges, with respect to the base refractive power direction, that the evaluation criteria are satisfied as long as the corresponding difference is less than a few degrees, e.g., less than 1°. If these evaluation criteria are all satisfied, the eyeball model construction unit 12 adopts the toric surface assuming the base curvature, the cross curvature and the direction along which the base curvature is assumed, having been set, as a model for the anterior or the posterior surface of the cornea. If any of the evaluation criteria are not satisfied, the eyeball model construction unit 12 executes evaluation by setting different values for the base curvature, the cross curvature and the direction along which the base curvature is assumed.

It is to be noted that an eyeglass lens corresponding to the prescription data may be set to the front of the eyeball, a ray of plane-wave light traveling from a point located frontward relative to the eyeglass lens toward the optical center of the eyeglass lens may be traced and parameters such as the curvatures of the cornea anterior surface 360a and the cornea posterior surface 360p may be determined through an iterative algorithm so as to achieve a refractive power of less than 0.02 D at the retina central position 320. Accordingly, more precise model construction can be achieved in a reflection of ocular examination condition.

Variation 3

A program that enables the information processing functions of the image creation device 1 may be recorded in a computer-readable recording medium and the program enabling control of the image creation processing described earlier and processing related to the image creation processing, recorded in the recording medium, may be read into a computer system and executed in the computer system. It is to be noted that the "computer system" in this context includes an OS (Operating System) and peripheral device hardware. In addition, the term "computer-readable recording medium" is used to refer to a portable recording medium such as a flexible disk, a magneto-optical disk, an optical disk or a memory card or a storage device such as a hard disk built into the computer system. Furthermore, the term "computer-readable recording medium" may refer to a medium that dynamically holds the program over a short period of time, examples of which include a network such as the Internet or a telephone network, via which the program is transmitted, or a medium that holds a program over a specific length of time, such as a volatile memory in a computer system functioning as a server or a client. In addition, the program described above may only fulfill some of the functions explained earlier, and the functions explained earlier may be fulfilled in conjunction with a program pre-installed in the computer system.

Figure 14:
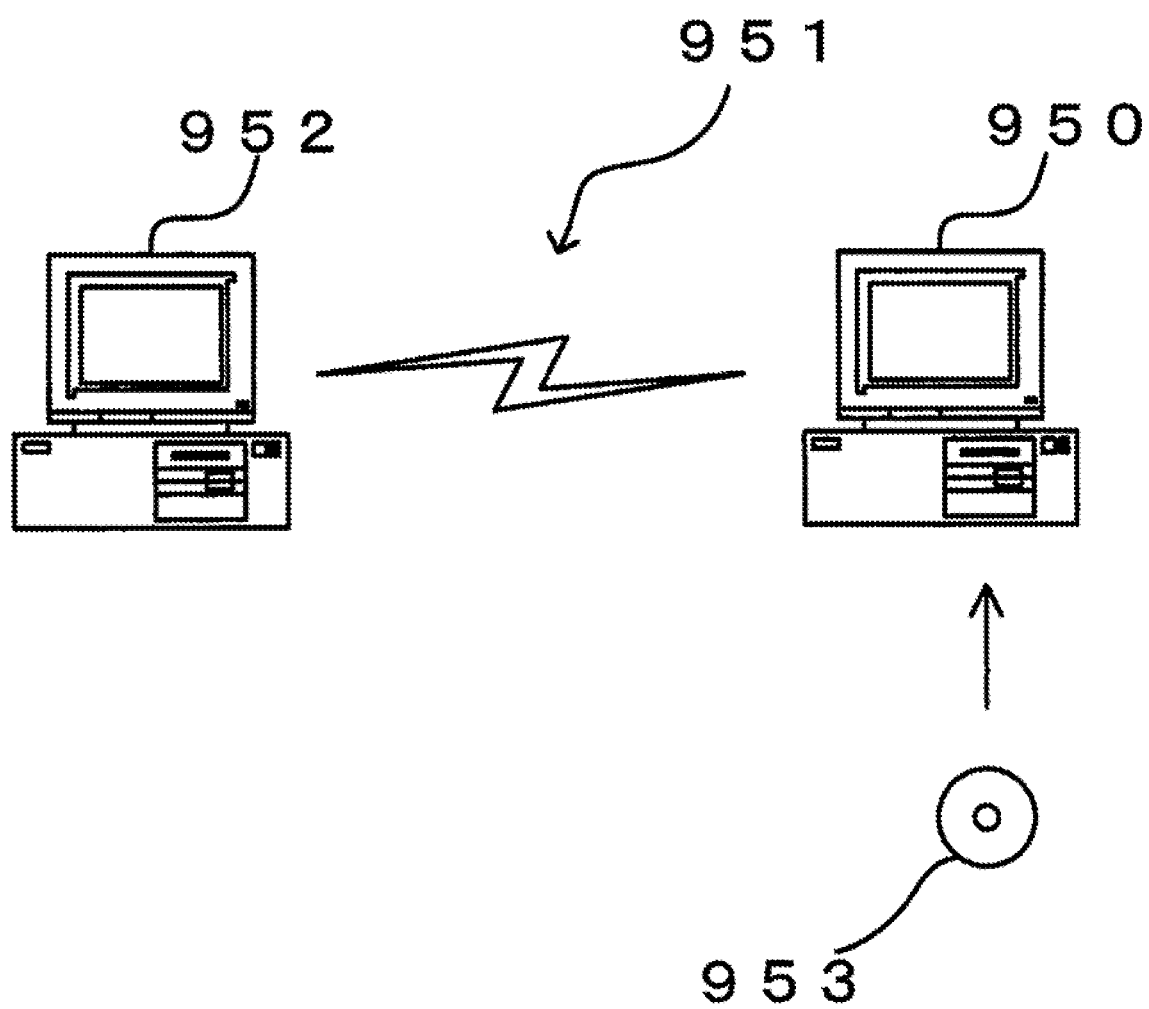
FIG. 14 is a conceptual diagram pertaining to a program enabling processing to be executed in an image creation device in an embodiment

Moreover, the present invention may be adopted in a personal computer (hereafter will be referred to as PC) or the like, by providing the program related to the control described above in a recording medium such as a CD-ROM or as a data signal transmitted on the Internet or the like. FIG. 14 shows how the program may be provided. A PC 950 receives the program via a CD-ROM 953. The PC 950 also has a function that enables it to connect with a communication line 951. A computer 952 is a server computer that provides the program stored in a recording medium such as a hard disk. The communication line 951 may be a communication network such as the Internet or a personal computer communication network or it may be a dedicated communication line. The computer 952 reads out the program from the hard disk and transmits the program to the PC 950 via the communication line 951. Namely, the program achieved as a data signal and carried on a carrier wave is transmitted via the communication line 951. In short, the program can be distributed as a computer-readable computer program product in any of various modes including a recording medium and a carrier wave.

The program that enables the information processing functions described above may be an image creation program that enables a computer to execute retina image creation processing through which retina images 70 of an outside world model 5 virtually viewed by a wearer through eyeglass lenses, projected onto retinas 32 of the eyes of the wearer, are created based upon outside world description data related to positions, shapes and optical characteristics of objects 53 within the outside world model 5, eyeglass lens description data related to positions, shapes and optical characteristics of the eyeglass lenses, and eyeball description data related to positions, shapes and optical characteristics of the eyes of the wearer virtually viewing the outside world model 5 through the eyeglass lenses.

The present invention is not limited to the particulars of the embodiment described above. Any other modes conceivable within the scope of the technical teachings of the present invention are within the scope of the present invention.

REFERENCE SIGNS LIST

1 . . . image processing device, 5 . . . outside world model, 10 . . . control unit, 11 . . . outside world model construction unit, 12 . . . eyeball model construction unit, 13 . . . eyeglass lens model construction unit, 14 . . . retina image creation unit, 15 . . . ray tracing unit, 17 . . . corresponding point calculation unit, 18 . . . binocular view image creation unit, 19 . . . moving image creation unit, 21 . . . display unit, 30 . . . eyeball model, 31 . . . crystalline lens, 32 . . . retina, 33 . . . crystalline lens edge, 34 . . . crystalline lens core, 35 . . . pupil, 36 . . . cornea, 70 . . . retina image, 71 . . . binocular view image, 330a . . . crystalline lens anterior surface, 330p . . . crystalline lens posterior surface, 340a . . . crystalline lens core anterior surface, 340p . . . crystalline lens core posterior surface

The invention claimed is:

1. An image creation device, comprising at least one processor configured to: create a retina image based upon:
target scene three-dimensional information related to a position, a shape, and optical characteristics of a structural object present in a virtual target scene,
eyeglass lens three-dimensional information related to a position, a shape, and optical characteristics of an eyeglass lens, and
eyeball three-dimensional information related to a position, a shape, and optical characteristics of an eye of a wearer viewing the virtual target scene through the eyeglass lens used as a virtual lens;
calculate corresponding points in retina images of two eyes based upon correlation coefficients (Dcorr) with respect to, luminance values (fl(xi, yj)) at pixels in a first pixel region where a plurality of pixels are present, set in the retina image for one eye, and luminance values (fr(xi, yj)) at pixels in a second pixel region where a plurality of pixels are present, set in the retina image for another eye, the corresponding points corresponding to a position within the virtual target scene;
calculate a binocular disparity with respect to the position based upon the corresponding points; and
create a composite image by using the retina images for the two eyes based upon the binocular disparity and a disparity correction parameter that includes a fusion ratio,
wherein the retina image is a virtual image projected onto a retina of the eye of the wearer viewing the virtual target scene through the eyeglass lens, and
wherein the correlation coefficients are determined as follows:

$$D_{corr} = \frac{\sum_{i=0}^{n}\sum_{j=0}^{n}(f_l(x_i, y_j) - \overline{f_l})(f_r(x_i + dx, y_j + dy) - \overline{f_r})}{\sqrt{\sum_{i=0}^{n}\sum_{j=0}^{n}(f_l(x_i, y_j) - \overline{f_l})^2}\sqrt{\sum_{i=0}^{n}\sum_{j=0}^{n}(f_r(x_i + dx, y_j + dy) - \overline{f_r})^2}}$$

wherein dx and dy are offset values, and fl and fr with macrons each represent an average of the luminance values in the first pixel region and the second pixel region, respectively.

2. The image creation device according to claim 1, wherein the at least one processor is further configured to control a display to display a distribution of the binocular disparity, which corresponds to the retina images.

3. The image creation device according to claim 1, wherein the at least one processor is further configured to create the retina image projected onto each retina of the eye based upon corrective lens three-dimensional information related to a position, a shape and optical characteristics of a corrective lens.

4. The image creation device according to claim 1, wherein the at least one processor is further configured to calculate an entry direction along which, and an entry position at which a ray of light entering the retina of the eye at each position, enters an anterior surface of a cornea of the eye and calculate a light path along which the ray of light, having departed the target scene, passes through the anterior surface of the cornea and arrives at the position in the retina, and a luminance value at a pixel corresponding to the position in the retina, based upon the entry direction and the entry position.

5. The image creation device according to claim 1, wherein the at least one processor is further configured to calculate the shape and the optical characteristics of the eye of the wearer based upon prescription data pertaining to the wearer.

6. The image creation device according to claim 5, wherein the at least one processor is further configured to calculate the shape of the eye based upon accommodation ability and a pupil diameter of the wearer.

7. The image creation device according to claim 1, wherein the at least one processor is further configured to control a display to display the retina image, or a composite image created by using the retina images for two eyes, as a moving image based upon a change occurring in the eyeball three-dimensional information.

8. The image creation device according to claim 5, wherein: the at least one processor is further configured to calculate a parameter with respect to an eyeball structure of the wearer based upon the prescription data pertaining to the wearer.

9. The image creation device according to claim 1, wherein $$\overline{f_l} = \frac{\sum_{i=0}^{n}\sum_{j=0}^{n}f_l(x_i, y_j)}{n^2} \text{ and } \overline{f_r} = \frac{\sum_{i=0}^{n}\sum_{j=0}^{n}f_r(x_i + dx, y_j + dy)}{n^2}$$

10. A method for image creation, comprising: creating a retina image based upon:
target scene three-dimensional information related to a position, a shape and optical characteristics of a structural object in a virtual target scene,
eyeglass lens three-dimensional information related to a position, a shape and optical characteristics of an eyeglass lens, and eyeball three-dimensional information related to a position, a shape and optical characteristics of an eye of a wearer viewing the virtual target scene through the eyeglass lens;
calculating corresponding points in retina images of two eyes based upon correlation coefficients (Dcorr) with respect to, luminance values (fl(xi, yj)) at pixels in a first pixel region where a plurality of pixels are present, set in the retina image for one eye, and luminance values (fr(xi, yj)) at pixels in a second pixel region where a plurality of pixels are present, set in the retina image for another eye, the corresponding points corresponding to a position within the virtual target scene;
calculating a binocular disparity with respect to the position based upon the corresponding points; and
creating a composite image by using the retina images for the two eyes based upon the binocular disparity and a disparity correction parameter that includes a fusion ratio, wherein the retina image is an image of the virtual target scene viewed by the wearer through the eyeglass lens, projected onto a retina of the eye of the wearer, and wherein the correlation coefficients are determined as follows:

$$D_{corr} = \frac{\sum_{i=0}^{n}\sum_{j=0}^{n}(f_l(x_i, y_j) - \overline{f_l})(f_r(x_i + dx, y_j + dy) - \overline{f_r})}{\sqrt{\sum_{i=0}^{n}\sum_{j=0}^{n}(f_l(x_i, y_j) - \overline{f_l})^2}\sqrt{\sum_{i=0}^{n}\sum_{j=0}^{n}(f_r(x_i + dx, y_j + dy) - \overline{f_r})^2}}$$

wherein dx and dv are offset values, and fl and fr with macrons each represent an average of the luminance values in the first pixel region and the second pixel region, respectively.

11. The method for image creation according to claim 10, wherein the disparity correction parameter sets an extent by which the binocular disparity of the two eyes is to be corrected.

12. A non-transitory computer-readable recording medium containing executable program instructions that, when executed by a computer, cause the computer to execute:

retina image creation processing through which a retina image is created based upon: target scene three-dimensional information related to a position, a shape and optical characteristics of a structural object in a virtual target scene, eyeglass lens three-dimensional information related to a position, a shape and optical characteristics of an eyeglass lens, and eyeball three-dimensional information related to a position, a shape and optical characteristics of an eye of a wearer viewing the virtual target scene through the eyeglass lens;

corresponding points calculating processing through which corresponding points in retina images of two eyes are calculated based upon correlation coefficients (Dcorr) with respect to luminance values (fl(xi, yj)) at pixels in a first pixel region where a plurality of pixels are present, set in the retina image for one eye, and luminance values (fr(xi, yj)) at pixels in a second pixel region where a plurality of pixels are present, set in the retina image for another eye, the corresponding points corresponding to a position within the virtual target scene;

binocular disparity calculating processing through which a binocular disparity with respect to the position is calculated based upon the corresponding points; and composite image creating processing through which a composite image is created by using the retina images for the two eyes based upon the binocular disparity and a disparity correction parameter that includes a fusion ratio, wherein the retina image is an image of the virtual target scene viewed by the wearer through the eyeglass lens, projected onto a retina of the eye of the wearer, and wherein the correlation coefficients are determined as follows:

$$D_{corr} = \frac{\sum_{i=0}^{n}\sum_{j=0}^{n}(f_l(x_i, y_j) - \overline{f_l})(f_r(x_i + dx, y_j + dy) - \overline{f_r})}{\sqrt{\sum_{i=0}^{n}\sum_{j=0}^{n}(f_l(x_i, y_j) - \overline{f_l})^2}\sqrt{\sum_{i=0}^{n}\sum_{j=0}^{n}(f_r(x_i + dx, y_j + dy) - \overline{f_r})^2}}$$

wherein dx and dv are offset values, and fl and fr with macrons each represent an average of the luminance values in the first pixel region and the second pixel region, respectively.

13. A method for designing an eyeglass lens, the method comprising:

designing an eyeglass lens based upon the shape of the eyeglass lens used by the image creation device according to claim 1, to create the retina image.

14. A method for manufacturing an eyeglass lens, the method comprising:

designing the eyeglass lens through the method for designing an eyeglass lens according to claim 13; and manufacturing the eyeglass lens having been designed through the method for designing an eyeglass lens.

* * * * *

UNITED STATES PATENT AND TRADEMARK OFFICE
CERTIFICATE OF CORRECTION

PATENT NO. : 10,958,898 B2
APPLICATION NO. : 16/389428
DATED : March 23, 2021
INVENTOR(S) : Takeshi Kishimoto It is certified that error appears in the above-identified patent and that said Letters Patent is hereby corrected as shown below:

In the Claims

Column 21, Line 27 (approx.), In Claim 1, delete "to," and insert -- to --, therefor.

Column 22, Line 40 (approx.), In Claim 9, after "$\bar{f_l} = \frac{\sum_{i=0}^{n}\sum_{j=0}^{n} f_l(x_i, y_j)}{n^2}$ and $\bar{f_r} = \frac{\sum_{i=0}^{n}\sum_{j=0}^{n} f_r(x_i + dx, y_j + dy)}{n^2}$," insert -- . --.

Column 22, Line 55, In Claim 10, delete "to," and insert -- to --, therefor.

Column 23, Line 15, In Claim 10, delete "dv" and insert -- dy --, therefor.

Column 24, Line 28 (Approx.), In Claim 12, delete "dv" and insert -- dy --, therefor.

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*